United States Patent [19]
Bigg et al.

[11] Patent Number: 5,981,542
[45] Date of Patent: Nov. 9, 1999

[54] CAMPTOTHECIN ANALOGUES, PREPARATION METHODS THEREFOR, USE THEREOF AS DRUGS, AND PHARMACEUTICAL COMPOSITIONS CONTAINING SAID ANALOGUES

[75] Inventors: Dennis Bigg, Gif-sur-Yvette; Olivier Lavergne, Massy, both of France; Francesc Pla Rodas, Santa Coloma de Farners, Spain; Jacques Pommier, Colombes; Gerard Ulibarri, Bures-sur-Yvette, both of France

[73] Assignee: Societe de Conseils de Recherches et d'Applications Scientifiques (S.C.R.A.S.), France

[21] Appl. No.: 08/973,561

[22] PCT Filed: Jun. 21, 1996

[86] PCT No.: PCT/FR96/00980

§ 371 Date: Dec. 2, 1997

§ 102(e) Date: Dec. 2, 1997

[87] PCT Pub. No.: WO97/00876

PCT Pub. Date: Jan. 9, 1997

[30] Foreign Application Priority Data

Jun. 21, 1995 [GB] United Kingdom .................. 9512670

[51] Int. Cl.$^6$ ...................... C07D 491/14; C07D 491/22; C07D 471/04; A61K 31/47
[52] U.S. Cl. .............................. 514/283; 514/280; 546/48
[58] Field of Search .............................. 546/48; 514/280, 514/283

[56] References Cited

FOREIGN PATENT DOCUMENTS

WO 94/11376    5/1994    WIPO .

OTHER PUBLICATIONS

Journal of Medicinal Chemistry, vol. 32, No. 3, 1989 pp. 715–720.
Journal of Medicinal Chemistry, vol. 19, No. 5, May 1976 pp. 675–679.

*Primary Examiner*—Mukund J. Shah
*Assistant Examiner*—Bruck Kifle
*Attorney, Agent, or Firm*—Bierman, Muserlian and Lucas

[57] ABSTRACT

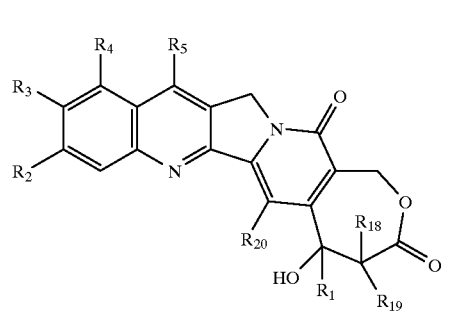

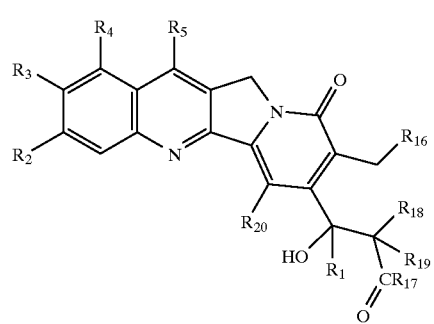

A camptothecin analog characterized in that the hydroxy lactone of the camptothecin is a β-hydroxy lactone or the corresponding β-hydroxyacid, resulting from the opening of said lactone, or a derivative of said β-hydroxyacid, or a Pharmaceutically acceptable salt thereof, is disclosed. In particular, compounds of formulae (I) and (II) are disclosed. Methods for preparing the compounds of formulae (I) and (II), pharmaceutical compositions containing said containing said compounds, and their use, particularly as topoisomerase inhibitors and antitumoral drugs, are also disclosed.

13 Claims, No Drawings

CAMPTOTHECIN ANALOGUES, PREPARATION METHODS THEREFOR, USE THEREOF AS DRUGS, AND PHARMACEUTICAL COMPOSITIONS CONTAINING SAID ANALOGUES

Camptothecin is a natural compound that was isolated for the first time from the leaves and the bark of the Chinese plant called *camptotheca acuminata* (see Wall et al., J. Amer. Chem. Soc. 88: 3888 (1966)). Camptothecin is a pentacyclic compound comprised of an indolizino [1,2-b] quinoline fragment fused with a six chained α-hydroxylactone. The carbon in position 20, which carries the α-hydroxy, is asymmetric and confers a rotational capacity to the molecule. The natural form of camptothecin possesses the absolute "S" configuration to the carbon 20 and complies with the following formula:

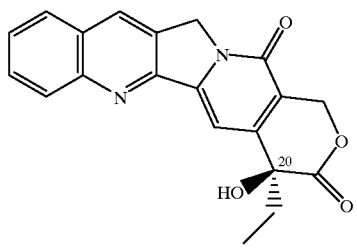

Camptothecin presents an anti-proliferating activity in several cancerous cellular lines, comprising the cellular lines of human tumors of the colon, of the lung and of the breast (Suffness, M. et al., The Alkaloids Chemistry and Pharmacology, Bross, A., ed., Vol. 25, p. 73 (Academic Press, 1985)). It is suggested that the anti-proliferating activity of camptothecin is in relation to its inhibiting activity of topoisomerase I of DNA.

It was indicated that the α-hydroxylactone was an absolute necessity both for in vivo and in vitro activity of the camptothecin (Camptothecins: New Anticancer Agents, Putmesil, M. et al., ed., p. 27 (CRC Press. 1995); Wall, M. et al., Cancer Res. 55: 753 (1995); Hertzberg et al., J. Med. Chem. 32: 715 (1982) and Crow et al., J. Med. Chem. 35: 160 (1992)). The present invention concerns a new class of camptothecin compounds, in which a β-hydroxylactone replaces the natural α-hydroxylactone of the camptothecin. The compounds according to the present invention exhibit powerful biological activity which is unexpected with respect to prior art.

Thus the invention has as its object new compounds of camptothecin which differ from all known compounds of camptothecin, in the sense that they contain a β-hydroxylactone (or its open hydroxycarboxylic form) in place of an α-hydroxylactone (or its open hydroxycarboxylic form); or a pharmaceutically acceptable salt of the latter. By compound of camptothecin it is understood a compound presenting the same structural skeleton as that of camptothecin (that is to say an indolizino [1,2-b] quinoline fragment that is fused to a six chained α-hydroxylactone), with or without other chemical substitutions on the skeletal structure (for example the camptothecin compounds). Different camptothecin compounds are well known by specialists, as described below. By β-hydroxylactone is meant a lactone that is comprised of a supplementary carbon atom between the carbon of the carboxyl and the α-carbon carrying the hydroxy group on the α-hydroxylactone. The β-hydroxylactone of seven "closed" or "open" chains, in which the ester bond between the carbonyl group and the adjacent oxygen atom is hydrolized, which shows by the formation of a carboxylic acid group and a hydroxyl group, which groups may or may not be substituted.

A compound of camptothecin according to the invention may then comprise substitutions on the indolizino [1,2-5] quinoline fragment (for example to improve the solubility of the compound) or on the open or closed β-hydroxylactone (for example to improve the stability of the compound). The examples of substitutions on closed β-hydroxylactone are comprised of an alkyl substitution (for example ethyl) on the β-carbon. The examples of substitution on the open β-hydroxylactone are comprised of an alkyl substitution on the β-carbon, substitutions (for example an amidation) on the carboxylic acid result, and the substitutions (for example an esterification) or suppressions of a hydroxyl group result.

The invention has more particularly for subject matter compounds of formula (I) and of formula (II),

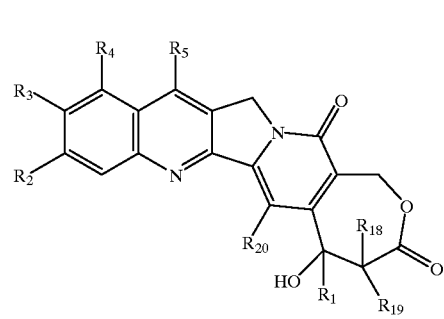

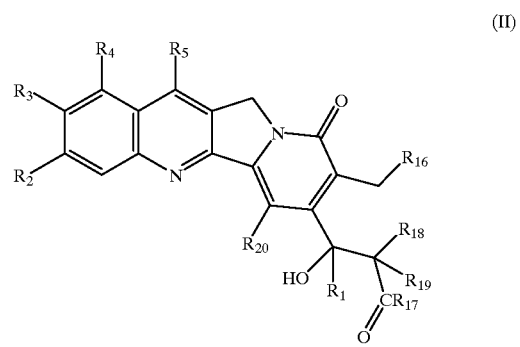

in racemic form, enantiomer or any combination of these forms, in which $R_1$ represents a lower alkyl, a lower alkenyl, a lower alkynyl, a lower haloalkyl, and lower alkoxy lower alkyl or a lower alkylthio lower alkyl;

$R_2$, $R_3$, and $R_4$ represent, independently, H, halo, lower halo alkyl, lower alkyl, lower alkenyl, cyano, lower cyano alkyl, nitro, lower nitro alkyl, amido, lower amido alkyl, hydrazino, lower hydrazino alkyl, azido, lower azido alkyl, $(CH_2)_m NR_6 R_7$, $(CH_2)_m OR_6$, $(CH_2)_m SR_6$, $(CH_2)_m CO_2 R_6$, $(CH_2)_m NR_6 C(O)R_8$, $(CH_2)_m C(O)R_8$, $(CH_2)_m OC(O)R_8$, $O(CH_2)_m NR_6 R_7$, $OC(O) NR_6 R_7$, $OC(O)(CH_2)_m CO_2 R_6$, or $(CH_2)_n [N=X]$, $OC(O)[N=X]$, $(CH_2)_m OC(O)[N=X]$ (in which [N=X], in this invention represents a heterocyclic group of 4 to 7 chains with the nitrogen atom N, which is a member of the heterocyclic group, and X represents the resulting members, necessary to complete the heterocyclic group, selected from among the group comprised of O, S, $CH_2$, CH, N, $NR_9$ and $COR_{10}$), aryl or lower aryl alkyl substituted (that is to say, substituted one to four times on the heterocyclic or aryl group) or not substituted, in which the substituent is a lower alkyl, halo, nitro, amino, lower alkylamino, lower haloalkyl, lower hydroxy alkyl, lower alkoxy, or lower alkoxy lower alkyl) or $R_2$ and $R_3$ form together a chain of 3 or 4 links, in which the elements of the chain are selected from among the group comprised of CH, $CH_2$, O, S, N or $NR_9$;

$R_5$ represents H, halo, lower halo alkyl, lower alkyl, lower alkoxy, lower alkoxy lower alkyl, lower alkylthio lower alkyl, cycloalkyl, lower cycloalkyl alkyl, cyano, cyano alkyl, lower alkyl lower sulphonyl alkyl, lower hydroxy alkyl, nitro, $(CH_2)_mC(O)R_8$, $(CH_2)_mNR_6C(O)R_8$, $(CH_2)_mNR_6R_7$, $(CH_2)_mN(CH_3)(CH_2)_nNR_6R_7$, $CH_2)_mOC(O)R_8$, $(CH_2)_mOC(O)NR_6R_7$, $(CH_2)_mS(O)_qR_{11}$, $(CH_2)_mP(O)R_{12}R_{13}$, $(CH_2)_2P(S)R_{12}R_{13}$, or $(CH_2)_n[N=X]$, $OC(O)[N=X]$, $(CH_2)_mOC(O)[N=X]$, aryl or substituted lower aryl alkyl (that is to say one to four times on the aryl group or heteroaryl) or not substituted, in which the substituent is a lower alkyl, halo, nitro, amino, lower alkyl amino, lower halo alkyl, lower hydroxy alkyl, lower alkoxy or lower alkoxy lower alkyl;

$R_6$ and $R_7$ represent, independently, H, and lower alkyl, lower hydroxy alkyl, lower alkyl lower amino alkyl, lower amino alkyl, cycloalkyl, lower cycloalkyl alkyl, lower alkenyl, lower alkoxy lower alkyl, lower halo alkyl, or aryl or substituted lower aryl alkyl (that is to say one to four times on the aryl group) or non-substituted, in which the substituent is a lower alkyl, halo, nitro, amino, lower alkyl amino, lower halo alkyl, lower hydroxy alkyl, lower alkoxy, or lower alkoxy lower alkyl;

$R_8$ represents H, and lower alkyl, lower hydroxy alkyl, amino, lower alkyl amino, lower alkyl lower amino alkyl, lower amino alkyl, cycloalkyl, lower cycloalkyl alkyl, lower alkenyl, lower alkoxy, lower alkoxy lower alkyl, lower halo alkyl, or aryl or substituted lower aryl alkyl (that is to say, one to four times on the aryl group) or non-substituted, in which the substituent is a lower alkyl, halo, nitro, amino, lower alkyl amino, lower halo alkyl, lower hydroxy alkyl, lower alkoxy, or lower alkoxy lower alkyl;

$R_9$ represents H, a lower alkyl, lower halo alkyl, aryl, or substituted aryl by one or more groups chosen from among the lower radical alkyl, halo, nitro amino, lower alkyl amino, lower halo alkyl, lower hydroxy alkyl, lower alkoxy, or lower alkoxy lower alkyl;

$R_{10}$ represents H, a lower alkyl, lower halo alkyl, lower alkoxy, aryl or substituted aryl (that is to say, presenting one to four substituents on the aryl group) by one or more groups chosen from among the lower radical alkyl, lower halo alkyl, lower hydroxy alkyl, or lower alkoxy lower alkyl;

$R_{11}$ represents a lower alkyl, aryl, $(CH_2)_mOR_{14}$, $(CH_2)_mSR_{14}$, $(CH_2)_2NR_{14}R_{15}$ or $(CH_2)_m[N=X]$;

$R_{12}$ and $R_{13}$ represent, independently, a lower alkyl, aryl, lower alkoxy, aryloxy or amino;

$R_{14}$ and $R_{15}$ represent, independently, H, and lower alkyl or aryl;

$R_{16}$ represents H or $OR_{21}$;

$R_{17}$ represents $OR_6$ or $NR_6R_7$;

$R_{18}$ and $R_{19}$ represent, independently, H, halo, lower alkyl, lower alkoxy or hydroxy;

$R_{20}$ represents H or halo;

$R_{21}$ represents H, a lower alkyl, CHO or $C(O)(CH_2)_mCH_3$;

m is an integer comprised between 0 and 6;

n is 1 or 2; and q represents an integer from 0 to 2; and $[N=X]$ represents a heterocyclic group with 4 to 7 links, X representing the necessary chain to complete said heterocyclic group and selected from the group comprised of O, S, $CH_2$, CH, N, $NR_9$ and $COR_9$; or a pharmaceutically acceptable salt of the latter.

The invention has particularly as its subject matter the compounds of formula I and II such as defined above, in which $R_1$ represents a lower alkyl, lower alkenyl, lower halo alkyl, lower alkoxy lower alkyl or lower alkylthio lower alkyl; $R_5$ represents H, a halo, lower halo alkyl, lower alkyl, lower alkoxy lower alkoxy lower alkyl, lower alkylthio lower alkyl, cycloalkyl, lower cycloalkyl alkyl, cyano, cyano alkyl, lower hydroxy alkyl, nitro, $(CH_2)_mC(O)R_8$, $(CH_2)_mNR_6C(O)R_8$, $(CH_2)_mNR_6R_7$, $(CH_2)_mN(CH_3)(CH_2)_nNR_6R_7$, $(CH_2)_mOC(O)R_8$, $(CH2)_mOC(O)NR_6R_7$, or $(CH_2)_n[N=X]$, $OC(O)[N=X]$, $(CH_2)_mOC[N=X]$, aryl or lower aryl alkyl, substituted or not substituted; $R_{12}$ and $R_{13}$ represent, independently, a lower alkyl; $R_{16}$ represents $OR_{21}$; and $R_{18}$, $R_{19}$ and $R_{20}$ represent H.

The invention has more particularly as its subject matter the compounds of formula I and II as is defined above in which $R_1$ represents a lower alkyl, lower alkenyl, lower halo alkyl or lower alkoxy lower alkyl; $R_2$, $R_3$ and $R_4$ represent, independently, H, halo, lower halo alkyl, lower alkyl, nitro, amido, lower amido alkyl, hydrazino, lower hydrazino alkyl, azido, lower azido alkyl, $(CH_2)_mNR_6R_7$, $(CH_2)_mOR_6$, $(CH_2)_mSR_6$, $(CH_2)_mC(O)R_8$, $OC(O)NR_6R_7$, $(CH_2)_n[N=X]$, or $(CH_2)_mOC(O)[N=X]$ substituted or non-substituted, or $OC(O)[N=X]$; or $R_2$ and $R_3$, together form a chain of 3 or 4 links, in which said elements of the chain are chosen from the group comprised of CH, $CH_2$, O, S, N, or $NR_9$; $R_5$ represents H, halo, lower halo alkyl, lower alkyl, lower alkoxy, lower alkoxy lower alkyl, lower alkylthio lower alkyl, lower hydroxy alkyl, nitro, $(CH_2)_mC(O)R_8$, $(CH_2)_mNR_6C(O)R_8$, $(CH_2)_mNR_6R_7$, $(CH_2)_mN(CH_3)(CH_2)_nNR_6R_7$, $(CH_2)_mOC(O)R_8$, $(CH_2)_mOC(O)NR_6R_7$, $(CH_2)_n[N=X]$ or $OC(O)[N=X]$ substituted or non-substituted, or $(CH_2)_mOC(O)[N=X]$; $R_6$ and $R_7$ represent, independently, H, a lower alkyl, lower hydroxy alkyl, lower alkyl lower amino alkyl, lower amino alkyl, cycloalkyl, lower cycloalkyl alkyl, lower alkoxy lower alkyl, aryl, lower aryl alkyl or lower halo alkyl; $R_8$ represents H, and lower alkyl, lower hydroxy alkyl, lower alkyl amino, lower alkyl lower amino alkyl, lower amino alkyl, cycloalkyl, lower cycloalkyl alkyl, lower alkenyl, lower alkoxy, lower alkoxy lower alkyl, lower halo alkyl, aryl or lower aryl alkyl; $R_9$ represents H, a lower alkyl, or a lower halo alkyl; $R_{10}$ represents H, and lower alkyl, lower halo alkyl, or a lower alkoxy; $R_{11}$ represents and lower alkyl; and $R_{14}$ and $R_{15}$ represent, independently, H or a lower alkyl.

The invention has more particularly as its subject matter the compounds of formula I such as is defined in which $R_1$ represents the ethyl group; $R_2$ and $R_3$ represent, independently, H, a lower alkyl, halo, lower halo alkyl or $(CH_2)_mOR_6$, or $R_2$ and $R_3$, together, form a methylenedioxy or an ethylenedioxy; and $R_4$ and $R_5$ represent, independently, H, and lower alkyl, $(CH_2)_mNR_6R_7$ or $(CH_2)_n[N=X]$ non-substituted or substituted by a lower alkyl. Preferably, $R_4$ represents H or $(CH_2)_mNR_6R_7$ in which $R_6$ and $R_7$ represent, independently, H or a lower alkyl, and $R_5$ represents H, and lower alkyl or $(CH_2)_n[N=X]$ substituted or non-substituted by a lower alkyl; as example of $[N=X]$ substituted or non-substituted, the piperidyl radical, morpholinyl, piperazinyl, imidazolyl and 4-methylpiperazinyl may be cited.

In a manner more preferable, $R_2$ represents H or a halo, and preferably H, chloro or fluoro; and $R_3$ represents H, a lower alkyl, halo or $OR_6$ in which $R_6$ represents H, a lower alkyl or a lower aryl alkyl, and preferably H, fluoro, chloro, methyl or methoxy. In an equally preferable manner, $R_2$ and $R_3$ form together a methylenedioxy or an ethylenedioxy.

More particularly, the invention has as its subject matter the products described hereafter in the examples, in particular the products corresponding to the following formulas:

5-ethyl-4,5-dihydro-5-hydroxy-1H-oxepino [3',4':6,7]-indolizino [1,2-b] quinoline-3,15 (4H, 13H)-dione 5,12-diethyl-4,5-dihydro-5-hydroxy-1H-oxepino [3',4': 6,7]-indolizino [1,2-b] quinoline-3,15 (4H,13H)-dione 8-ethyl-2,3,8,9-tetrahydro-8-hydroxy-10H,12H-[1,4] dioxino [2,3-g] oxepino [3',4':6,7] indolizino [1,2-b] quinoline-10,13 (15H)-dione 10-benzyloxy-5-ethyl-4,5-dihydro-5-hydroxy-1H-oxepino [3',4':6,7]-indolizino [1,2-b] quinoline-3,15 (4H,13H)-dione 5-ethyl-4,5-dihydro-5,10,-dihydroxy-1H-oxepino [3',4':6, 7]-indolizino [1,2-b] quinoline-3,15 (4H,13H)-dione 11-(dimethylamino)methyl-5-ethyl-4,5-dihydro-5,10-dihydroxy-1H-oxepino [3',4':6,7]-indolizino [1,2-b] quinoline-3,15 (4H,13H)-dione 5-ethyl-9-fluoro-4,5-dihydro-5-hydroxy-10-methoxy-1H-oxepino [3',4':6,7] indolizino [1,2-b] quinoline-3, 15(4H,13H)-dione 9-chloro-5-ethyl-4,5-dihydro-5-hydroxy-10-methyl-1H-oxepino [3',4':6,7] indolizino [1,2-b] quinoline-3,15 (4H,13H)-dione 5-ethyl-9,10-difluoro-4,5-dihydro-5-hydroxy-1H-oxepino [3',4':6,7] indolizino [1,2-b] quinoline-3,15 (4H,13H)-dione 7-ethyl-7,8-dihydro-7-hydroxy-9H,11H-[1,3] dioxole [4,5-g] oxepino [3',4 ':6,7] indolizino [1,2-b] quinoline-9,12(14H)-dione 9-chloro-5-ethyl-4,5-dihydro-5-hydroxy-10-methoxy-1H-oxepino [3',4':6,7] indolizino [1,2-b] quinoline-3, 15(4H,13H)-dione 5-ethyl-4,5-dihydro-5-hydroxy-10-methoxy-1H-oxepino [3',4':6,7] indolizino [1,2-b] quinoline-3,15(4H,13H)-dione 9,11-dichloro-5-ethyl-4,5-dihydro-5-hydroxy-1H-oxepino [3',4':6,7] indolizino [1,2-b] quinoline-3,15 (4H,13H)-dione 5-ethyl-9-fluoro-4,5-dihydro-5-hydroxy-10-methyl-1H-oxepino [3',4':6,7] indolizino [1,2-b] quinoline-3,15 (4H,13H)-dione 5-ethyl-10-fluoro-4,5-dihydro-5-hydroxy-1H-oxepino [3', 4':6,7] indolizino [1,2-b] quinoline-3,15(4H,13H)-dione 10-chloro-5-ethyl-4,5-dihydro-5-hydroxy-1H-oxepino[3', 4':6,7] indolizino [1,2-b] quinoline-3,15(4H,13H)-dione 10-chloro-5-ethyl-9-fluoro-4,5-dihydro-5-hydroxy-1H-oxepino [3',4':6,7] indolizino [1,2-b] quinoline-3,15 (4H,13H)-dione 5,12-diethyl-4,5-dihydro-5,10-dihydroxy-11-morpholino methyl-1H-oxepino [3',4':6,7] indolizino [1,2-b] quinoline-3,15(4H,13H)-dione 5,12-diethyl-9-fluoro-4,5-dihydro-5-hydroxy-10-methoxy-1H-oxepino [3',4':6,7] indolizino [1,2-b] quinoline-3,15(4H,13H)-dione 5-ethyl-4,5-dihydro-5-hydroxy-12-methyl-1H-oxepino [3',4':6,7]indolizino [1,2-b] quinoline-3,15 (4H,13H)-dione 9-chloro-5-ethyl-4,5-dihydro-5-hydroxy-10-methoxy-12-(4-methyl piperazinomethyl)-1H-oxepino [3',4':6,7] indolizino [1,2-b] quinoline-3,15(4H,13H)-dione 9-chloro-5-ethyl-4,5-dihydro-5-hydroxy-10-methoxy-12-morpholinomethyl-1H-oxepino [3',4':6,7] indolizino [1,2-b] quinoline-3,15(4H,13H)-dione 5-ethyl-4,5-dihydro-5-hydroxy-12-(4-methyl piperazinomethyl)-1H-oxepino [3',4':6,7] indolizino [1,2-b] quinoline-3,15(4H,13H)-dione 5-ethyl-4,5-dihydro-5-hydroxy-12-piperidinomethyl-1H-oxepino [3',4':6,7] indolizino [1,2-b] quinoline-3,15 (4H,13H)-dione 5-ethyl-4,5-dihydro-5-hydroxy-12-morpholinomethyl-1H-oxepino [3',4': 6,7] indolizino [1,2-b] quinoline-3, 15(4H,13H)-dione 5-ethyl-10-fluoro-4,5-dihydro-5-hydroxy-12-(4-methylpiperazinomethyl)-1H-oxepino [3',4':6,7] indolizino [1,2-b] quinoline-3,15(4H,13H)-dione 5-ethyl-10-fluoro-4,5-dihydro-5-hydroxy-12-morpholinomethyl-1H-oxepino [3',4':6,7] indolizino [1,2-b] quinoline-3,15(4H,13H)-dione 5-ethyl-9-fluoro-4,5-dihydro-5-hydroxy-10-methyl-12-(4-methylpiperazinomethyl)-1H-oxepino [3',4':6,7] indolizino [1,2-b] quinoline-3,15(4H,13H)-dione 5-ethyl-9-fluoro-4,5-dihydro-5-hydroxy-10-methyl-12-morpholinomethyl-1H-oxepino [3',4':6,7] indolizino [1,2-b] quinoline-3,15(4H,13H)-dione 5-ethyl-9-fluoro-4,5-dihydro-5-hydroxy-10-methyl-12-piperidinomethyl-1H-oxepino [3',4':6,7] indolizino [1,2-b] quinoline-3,15(4H,13H)-dione 8-ethyl-2,3,8,9-tetrahydro-8-hydroxy-16-(4-methyl piperazinomethyl)-10H, 12H-(1,4) dioxino (2,3-g) oxepino [3',4':6,7] indolizino [1,2-b] quinoline-10,13 [15H]-dione 9-chloro-5-ethyl-10-fluoro-4,5-dihydro-5-hydroxy-12-morpholinomethyl-1H-oxepino [3',4':6,7] indolizino [1,2-b] quinoline-3,15(4H,13H)-dione or a pharmaceutically acceptable salt of the latter.

The invention has more particularly for object equally the compounds of formula II as is described above, in which $R_1$ represents the ethyl group; $R_2$ and $R_3$ represent, independently, H, and lower alkyl, halo, lower halo alkyl, or $(CH_2)_mOR_6$, or $R_2$ and $R_3$ form together a methylenedioxy, or an etnylenedioxy; $R_4$ and $R_5$ represent, independently, H, and lower alkyl, $(CH_2)_mNR_6R_7$, or $(CH_2)_n[N=X]$ non-substituted or substituted by a lower alkyl; $R_{20}$ represents H and $R_{17}$ represents $OR_6$, in which $R_6$ represents H or a lower alkyl, or $NR_6R_7$ in which $R_6$ and $R_7$, independently represent H, and lower alkyl, aryl or lower aryl alkyl. Preferably $R_4$ represents H or $(CH_2)_mNR_6R_7$, in which $R_6$ and $R_7$ represent, independently, H or a lower alkyl; $R_5$ represents H, a lower alkyl, or $(CH_2)_n[N=X]$ non-substituted or substituted by a lower alkyl and $R_{17}$ represents $OR_6$ in which $R_6$ represents H or a lower alkyl; or a pharmaceutically acceptable salt of the latter. As example of [N=X] the piperidyl radical, morpholinyl, piperazinyl, imidazolyl and 4-methylpiperazinyl may be cited.

Even more preferable, $R_2$ represents H or halo and preferably H, chloro or fluoro; $R_3$ represents H, a lower alkyl, halo or $OR_6$ in which $R_6$ represents H, a lower alkyl or a lower aryl alkyl and preferably H, fluoro, chloro, methyl or methoxy. Equally as preferential, $R_2$ and $R_3$ form together methylenedioxy or ethylenedioxy.

More particularly, the invention has for object the products described hereafter in the examples, in particular the products responding to the following formulas:

tert-butyl β-ethyl-β-hydroxy-γ-(8-hydroxymethyl-9-oxo (11H)-indolizino-[1,2-b] quinoline-7-yl)-propionate ethyl β-ethyl-β-hydroxy-γ-(8-hydroxymethyl-9-oxo (11H)-indolizino-[1,2-b] quinoline-7-yl)-propionate β-ethyl-β-hydroxy-γ-(8-hydroxymethyl-9-oxo (11H)-indolizino-[1,2-b] quinoline-7-yl)-propionic acid methyl β-ethyl-β-hydroxy-γ-(8-hydroxymethyl-9-oxo (11H)-indolizino-[1,2-b] quinoline-7-yl)-propionate ethyl β-ethyl-α,α-difluoro-β-hydroxy-γ-(8-hydroxymethyl-9-oxo (11H)-indolizino-[1,2-b] quinoline-7-yl)-propionate ethyl β-ethyl-β-hydroxy-γ-(8-hydroxymethyl-9-oxo (11H)-indolizino-[1,2-b] quinoline-7-yl)-propionate tert-butyl β-ethyl-β-hydroxy-γ-(8-hydroxymethyl-9-oxo (11H)-indolizino-[1,2-b] quinoline-7-yl)-propionate β-ethyl-γ-(12-ethyl-8-hydroxymethyl-9-oxo (11H)-indolizino-[1,2-b] quinoline-7-yl)-β-hydroxy-propionic acid γ-(12-benzyloxy-8-hydroxymethyl-9-oxo (11H)-indolizino [1,2-b] quinoline-7-yl)-β-ethyl-β-hydroxy-propionic acid (E)

or a pharmaceutically acceptable salt of the latter.

Such as it is used here, the term lower in reference to alkyl, alkylthio and alkoxy groups designate the saturated aliphatic hydrocarbon groups, linear or branched, comprising 1 to 6 carbons, as for example methyl, ethyl, propyl, isopropyl, butyl, t-butyl, methylthio, ethylthio, methoxy, and ethoxy. In reference to the alkenyl or alkynyl groups, the term lower designates the groups comprising 2 to 6 carbon atoms and one or more double or triple bonds, as for example the vinyl, allyl, isopropenyl, pentenyl, hexanyl, propenyl ethynyl, propynyl and butynyl groups. The term cycloalkyl designates a cycle comprising 3 to 7 carbon atoms, as for example the cyclopropyl, cyclobutyl, cyclopentyl or cyclohexyl groups. The term aryl designates a hydrocarbon compound mono-, di- or tricyclic with at least one aromatic cycle, each cycle containing a maximum of 7 links, as for example phenyl, naphthyl, anthracyl, biphenyl or indenyl. The term halo signifies chloro, bromo, iodo, or fluoro. The radicals corresponding to the expressions lower halo alkyl, lower cyano alkyl, lower nitro alkyl, lower amido alkyl, lower hydrazino alkyl, lower azido alkyl, lower aryl alkyl, lower hydroxy alkyl, lower alkoxy lower alkyl, lower alkylthio lower alkyl, and lower alkyl sulphonyl lower alkyl are substituted, respectively, by one to three halo, cyano, nitro, amido, hydrazino, azido, aryl, hydroxy, lower alkoxy, lower alkylthio or lower sulphonyl groups. The lower alkyl amino radical may contain one or two lower alkyl groups, and represent for example $NHCH_3$, $NHCH_2CH_3$, $N(CH_3)_2$, or $N(CH_3)(CH_2CH_3)$. The examples of [N=X] comprise the piperidinyl, morpholinyl, piperizinyl and imidazolyl groups.

As is observed for camptothecin, the carbon atom carrying the hydroxy function on the β-hydroxylactone or the α-hydroxycarboxylate group of the compounds, according to the present invention, is asymmetrical. Consequently, the compounds according to the present invention have two possible enantiomer configurations, that is to say in the "R" and "S" configurations. The present invention includes the two enantiomer configurations and all the combinations of these configurations, comprising as well the "RS" racemic mixtures. In the interest of simplicity, when any specific configuration is not indicated in the structural formulas, it is understood that the two enantiomer configurations and their mixtures are represented.

The invention has as well as its subject matter the preparation procedures of the compounds of general formula I and II, either from camptothecin or from substituted camptothecin, or by total chemical synthesis.

The invention concerns thus a preparational procedure of formula I and II compounds, according to the invention starting from camptothecin or from substituted camptothecin characterized in that α-hydroxylactone of the camptothecin is reduced to the general formula

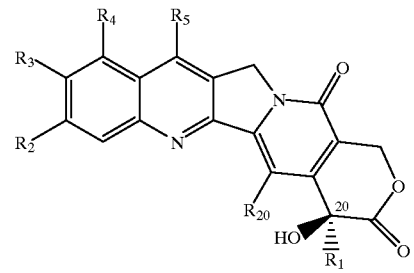

in which $R_1$, $R_2$, $R_3$, $R_4$, $R_5$ and $R_{20}$ have the significance indicated above, to obtain the α-hydroxylactol of general formula A

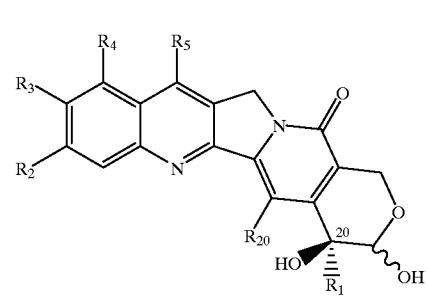

in which $R_1$, $R_2$, $R_3$, $R_4$, $R_5$ and $R_{20}$ have the significance indicated above.

In compound A thus formed, the carbon-carbon bond bonding the neighboring carbinol are cut by treatment with an appropriate oxydizing agent so as to result in a formula B compound

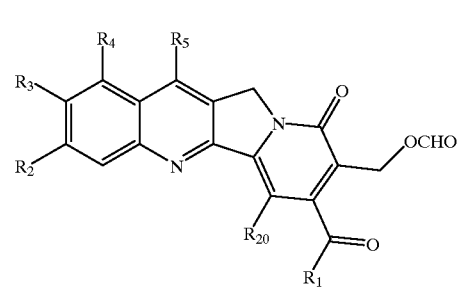

in which $R_1$, $R_2$, $R_3$, $R_4$, $R_5$ and $R_{20}$ have the significance indicated above.

It is subsequently treated with a functionalized alkylizing agent and the formyl functional group of the formula B compound is cut to give a β-hydroxyester of general formula C

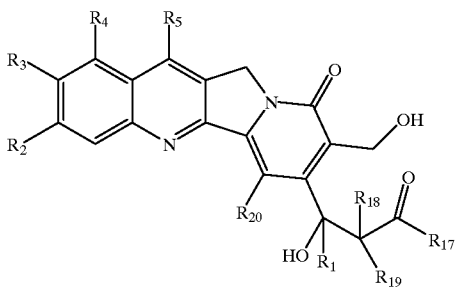

in which $R_1$, $R_2$, $R_3$, $R_4$, $R_5$, $R_{18}$, $R_{19}$, and $R_{20}$ have the significance indicated above and $R_{17}$ represents $OR_6$ and $R_6$ represents a lower alkyl, cycloalkyl, lower cycloalkyl alkyl, lower alkenyl, lower alkoxy lower alkyl or aryl or lower aryl alkyl;

said compound of general formula C is cyclized resulting in the β-hydroxylactonic compound of general formula D

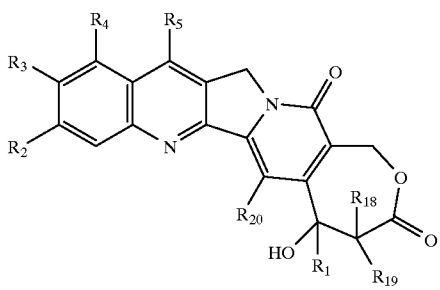

in which $R_1$, $R_2$, $R_3$, $R_4$, $R_5$, $R_{18}$, $R_{19}$ and $R_{20}$ have the significance indicated above, the lactone of general formula D is opened, resulting in the formula E compound

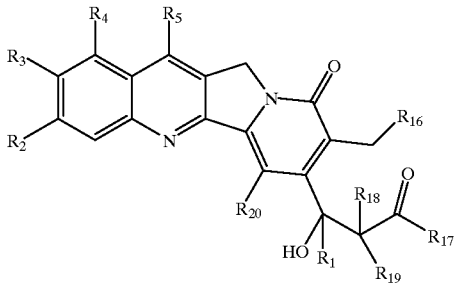

in which $R_1$, $R_2$, $R_3$, $R_4$, $R_5$, $R_{18}$, $R_{19}$ and $R_{20}$ have the significance indicated above; $R_{16}$ represents $OR_{21}$ in which $R_{21}$ represents H or a lower alkyl; and $R_{17}$ represents $OR_6$ or $NHR_6$ and $R_6$ represents H, a lower alkyl, cycloalkyl, lower cycloalkyl alkyl, lower alkenyl, lower alkoxy lower alkyl, or aryl or lower aryl alkyl.

Certain formula E compounds may be obtained as well by hydrolyzing the ester function of the corresponding formula C compounds. The general formula E compounds in which $R_{16}$ and/or $R_{17}$ represent, independently, the hydroxy radical, may be esterified or amidified under the classic conditions known by persons skilled in the art to obtain the esters or the amides corresponding to formula E.

In the above process, the $R_1$, $R_2$, $R_3$ and $R_4$ groups may be protected if necessary according to the classical methods of protection (Greene, T., Protective Groups in Organic Synthesis 10–86 (John Wiley & Sons 1981)). At the time of this procedure, the reduction occurs with the help of a reducing agent in an appropriate solvent such as, for example, sodium borohydride in methanol. The stage corresponding to the formation of compound B from compound A, is implemented under oxidizing conditions such as, for example, with lead tetraacetate, periodic acid or sodium metaperiodate in an appropriate solvent such as, for example, acetic acid. The treatment by a functionalized alkylizing agent may be implemented with the help of a metallic derivative for example lithium or zinc, or with the help of a carboxylic ester in an anhydrous aprotic solvent such as for example tetrahydrofurane. The stage of lactonisation that compound D to be obtained from compound C is generally carried out under acidic conditions, for example, by treatment with trifluoroacetic acid or hydrochloric gas dissolved in an anhydrous solvent such as dichloromethane or dioxane. The opening of the lactonic cycle of compound D to obtain compound E, may be done, for example, by hydrolysing under alkaline conditions followed by neutralization.

The examples of substituted camptothecins, used as starting products, may be found in the U.S. Pat. Nos. 4,473,692, 4,604,463, 4,894,956, 5,162,532, 5,395,939, 5,315,007, 5,264,579, 5,258,516, 5,254,690, 5,212,317, and 5,341,745, the PCT Patent Application Nos. US91/08028, US94/06451, US90/05172, US92/04611, US93/10987, US91/09598, EP94/03058 and EP95/00393 and the European Patent Applications Nos. 325 247, 495 432, 321 122 and 540 099.

The invention concerns as well a preparation procedure of the compounds of formula I and II, characterized in that compound of general formula M is coupled

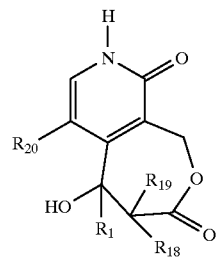

in which $R_1$, $R_{18}$ and $R_{19}$ have the significance indicated above and $R_{20}$ represents hydrogen or a halogen atom, with a 2-halo-3-quinoline-methanol of general formula N

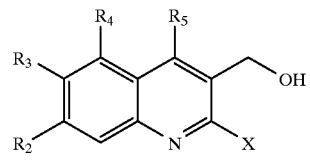

in which $R_2$, $R_3$, $R_4$ and $R_5$ have the significance indicated above and X represents a halogen atom, resulting in the formula O compound

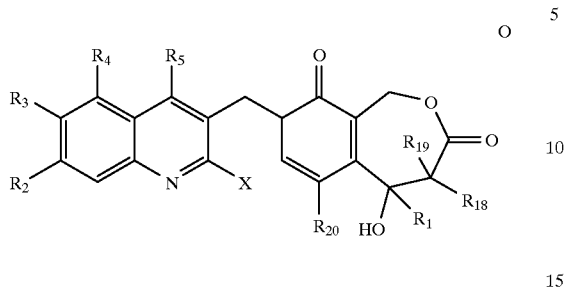

in which $R_1$, $R_2$, $R_3$, $R_4$, $R_5$, $R_{18}$, $R_{19}$, $R_{20}$ and X have the significance indicated above:

then the general formula O compound is cyclized to obtain the formula D compound such as is defined above.

In the above method, the $R_1$, $R_2$, $R_3$ and $R_4$ groups may be protected if necessary according to the classical methods of protection (Greene, T., Protective Groups in Organic Synthesis 10–86 (John Wiley & Sons 1981)). The formation of compound O from the general formula M and N compounds is carried out by a treatment known by persons skilled in the art by the name of Mitsunobu reaction (refer to Mitsunobu, O. et al., *Syntheses*, p.1 (1981)). It is comprised of displacing the hydroxyl function of compound N by a nucleophile such as compound M, or a deprotonated derivative of the latter, by treatment with a phosphine, for example triphenylphosphine, and azodicarboxylate derivative, for example diethyl azodicarboxylate, in an aprotic solvent such as, for example, tetrahydrofuran or N,N-dimethylformamide. The cyclisation of compound O occurs preferably in the presence of a pallidin catalyst (for example palladium diacetate) under basic conditions (provided for example by an alkaline acetate potentially combined with a phase transfer agent such as for example tetrabutylammonium bromide), in an aprotic solvent such as acetonitril or N,N-dimethylformamide, at a temperature between 50° C. and 120° C. (R. Grigg et al., *Tetrahedron* 46, page 4003 (1990)).

The general formula M compounds are new. They may be prepared according to a method characterized in that the carbonyl is protected of a pyridine of general formula

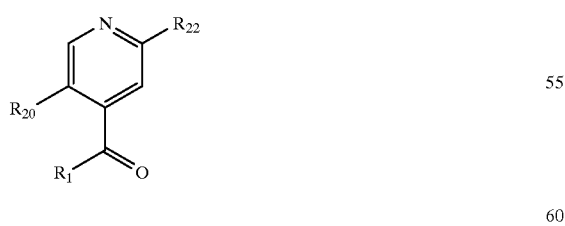

in which $R_1$ and $R_{20}$ have the significance indicated above and $R_{22}$ represents a halogen atom or a lower alkoxy, by an acetal function, resulting in the general formula F compound

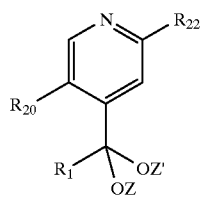

in which $R_1$, $R_{20}$ and $R_{22}$ have the significance indicated above and the Z and Z' groups represent, independently, a lower alkyl or form together a saturated hydrocarbon chain with 2 to 4 carbons:

a hydroxymethyl function is introduced into the general formula F compound, resulting in a general formula G compound

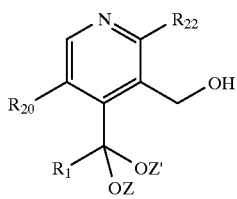

in which $R_1$, $R_{20}$, $R_{22}$, Z and Z' have the significance indicated above, subsequently the alcoholic function of the compound of general formula G is protected, resulting in the general formula H compound

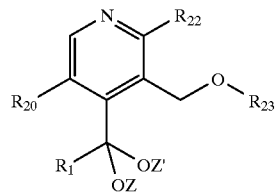

in which $R_1$, $R_{20}$, $R_{22}$, Z and Z' have the significance indicated above and $R_{23}$ represents a protector group of the alcohol group.

the acetal of the general formula H compound is unprotected, resulting in the general formula I' compound

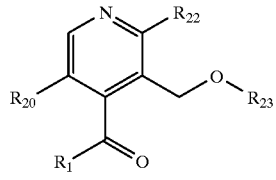

in which $R_1$, $R_{20}$, $R_{22}$, and $R_{23}$ have the significance indicated above, the formula I' compound is treated with a functionalized alkylizing agent, resulting in a β-hydroxyester of general formula J

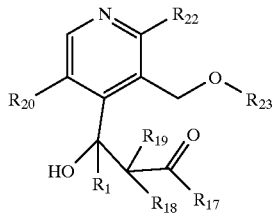

J in which $R_1$, $R_{20}$, $R_{22}$ and $R_{23}$ have the significance indicated above, $R_{18}$ and $R_{19}$ are as defined in the general formula II and $R_{17}$ represents $OR_6$ and $R_6$ represents a lower alkyl, cycloalkyl, lower cycloalkyl alkyl, lower alkenyl, lower alkoxy lower alkyl, or aryl or lower aryl alkyl;

the protector group $R_{23}$ is cleaved from the general formula J compound, resulting in a general formula K compound

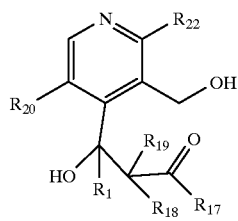

K in which $R_1$, $R_{18}$, $R_{19}$, $R_{20}$ and $R_{22}$ have the significance indicated above and $R_{17}$ represents $OR_6$ and $R_6$ represents a lower alkyl, cycloalkyl, lower cycloalkyl alkyl, lower alkenyl, lower alkoxy lower alkyl, or aryl or lower aryl alkyl;

general formula K compound is cyclized to form general formula L compound

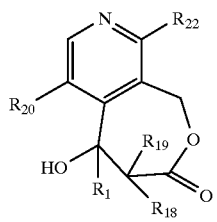

L in which $R_1$, $R_{18}$, $R_{19}$, $R_{20}$ and $R_{22}$ have the significance indicated above, and finally radical $R_{22}$ of the L compound is transformed into carbonyl, resulting in the general formula M compound

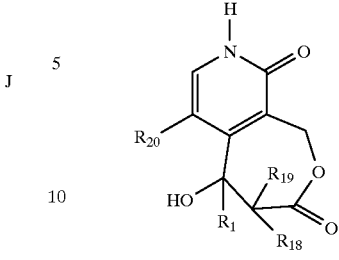

M in which $R_1$, $R_{18}$, $R_{19}$ and $R_{20}$ have the significance indicated above.

The carbonyl function of a 4-acyl-2-pyridine (obtained for example according to Lamattina, J. L., *J. Heterocyclic Chem.* 20, p. 553 (1983)) is preferably shielded by an acetal function, preferably a cyclic acetal, according to the classic conditions known by persons skilled in the art (Greene, T., Protective Groups in Organic Synthesis 10–86 (John Wiley & Sons 1981)). When R22 is chloro or fluoro, the intermediary thus obtained is treated by a sodium alcoholate or potassium alcoholate in an aprotic solvent (for example acetonitrile), or in the alcohol from which the alcoholate is derived, at a temperature between 0° C. and 100° C. resulting in the general formula F compound. The latter may be lithiated in position 3 by treatment with an aryl- or alkyl-lithium (for example mesityl-lithium) in a ethered solvent such as tetrahydrofurane at a temperature between −100° C. and 0° C. A formylizing electrophile such as N,N-dimethylformamide is added to the lithiated intermediary thus obtained, and the resulting aldehyde, after hydrolysis, is treated with a reducing agent such as sodium borohydride resulting in the general formula G compound. The shielding of the alcohol function of compound G is carried out according to classical conditions known by persons skilled in the art, resulting in a general formula H compound. The examples of the protector groups of the alcohol are comprised of those that form the ethers [for example methyl, methoxymethyl, tetrahydropyranyl, 2-methoxyethoxy methyl, benzyloxymethyl, t-butyl, and benzyl (substituted or not)], and the esters (for example formate, acetate and isobutyrate). For other examples of other primary hydroxyl protector groups, refer to Greene, T., Protectives Groups in Organic Synthesis. 10–86 (John Wiley & Sons, 1981). The unshielding of the general formula H compounds resulting in the general formula I' compound is performed in selective environments maintaining the integrity of the $R_{23}$ radical, for example, by treatment in acidic conditions (for example with trifluoroacetic acid). The selective conditions of protecting and unprotecting the functional groups are known by persons skilled in the art (Greene, T., Protective Groups in Organic Synthesis 10–86 (J. Wiley & Sons 1981)). The treatment of the I' compound by a functionalized alkylizing agent resulting in a general formula J β-hydroxyester, may be realized with the help of a lithium enolate or a zinc derivative of a carboxylic ester in an anhydrous aprotic solvent, for example tetrahydrofuran. The protector group $R_{23}$ of the general formula J compound, is cleaved resulting in the general formula K compound, under the unprotected conditions known by persons skilled in the art. For example, when $R_{23}$ is a benzyl group, an alcoholic solution of general formula J compound plus a palladium catalyzer may be subjected to a hydrogen atmosphere of 0.5 to 10 bars. The cyclization of the general formula K compound thus obtained may be brought into acidic conditions (for example treatment with trifluoroacetic acid, or hydrochloric gas dissolved in an anhydrous solvent such as dichloromethane or dioxane) resulting in a β-hydoxylactonic cycle with seven links such as in the general formula L compound. The general formula L compounds may be transformed into pyridones of general formula M, for example, by a hot hydrochloric acid treatment, or with a trimethylsilyle iodide.

The 2-halo-3-quinoline-methanol of general formula N may be obtained from the acetanilides of general formula P

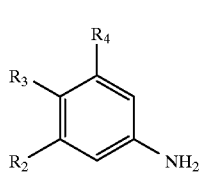

P in which $R_2$, $R_3$ and $R_4$ have the significance indicated in the general formulas of compounds I and II. In the procedures hereafter, the $R_2$, $R_3$ and $R_4$ groups may be protected if necessary according to the classical methods of protection (Greene, T., Protective Groups in Organic Synthesis 10–86 (John Wiley & Sons 1981)).

Formula N compounds may then be obtained according to the following procedure: said anilines of formula P are N-acetylated by treatment with an acetylizing agent such as for example acetic anhydride. The acetanilides thus obtained are treated at a temperature between 50° C. and 100° C., preferably 75° C., by a reagent known by persons skilled in the art under the reagent name Vilsmeyer (obtained by the action of phosphoryl oxychloride on N,N-dimethylformamide at a temperature between 0° C. and 10° C.) resulting in corresponding 2-chloro-3-quinolinecarbaldehyde (refer to, for example Meth-Cohn. et al., *J. Chem. Soc., Perkin Trans.* 1 p. 1520 (1981); Meth-Cohn, et al.,*J. Chem. Soc., Perkin Trans.* 1 p. 2509 (1981); and Nakasimhan et al., *J. Am. Chem. Soc.*, 112. p. 4431 (1990)). The chlorine on position 2 of the 2-chloro-3-quinolinecarbaldehydes may be substituted by iodine or by bromine by heating the product in an inert solvent such as acetonitrile in the presence of an iodine or bromine salt (for example sodium iodide or tetrabutylammonium bromide). A trace of acid such as concentrated hydrochloric acid may be necessary to catalyze this transformation. The 2-halo-3-quinolinecarbaldehydes are easily reduced to 2-halo-3-quinolinemethanols corresponding to the general formula N, under the classical conditions known by persons skilled in the art such as the treatment in an alcoholic solvent (for example methanol) by sodium borohydride at a temperature between 0° C. and 40° C.

Formula N compounds may be obtained as well according to the following procedure: the general formula P anilines such as are defined above are acylated by reacting with a nitrile (such as chloroacetonitrile or propionitrile) in the presence of boron trichloride and another Lewis acid such as aluminum trichloride, titanium tetrachloride or diethylaluminum chloride in an aprotic solvent or a mixture of an aprotic solvent, followed by a hydrolysis (cf. Sugasawa, T., et al.,*J. Am. Chem. Soc.* 100, p. 4842 (1978)). The resulting intermediate is then treated with ethylmalonyl chloride in an aprotic solvent such as acetonitrile in the presence of a base such as triethylamine, then treated by alkaline alcoholate, for example sodium methylate in methanol, resulting in an ethyl 2-hydroxy-3-quinolinecarboxylate substituted in position 4. The latter is transformed into ethyl 2-chloro-3-quinolinecarboxylate by treatment with a phosphoryloxy-chloride. When position 4 of the quinoline carries a chloromethyl group, a nucleophilic substitution may be carried out by treatment with a secondary amine such as for example dimethylamine, N-methylpiperazine, morpholine or piperidine. Ethyl 2-chloro-3-quinolinecarboxylate is then reduced by diisobutylaluminium hydride in an aprotic solvent such as dichloromethane resulting in 2-chloro-3-quinolinemethanol of general formula N. The analogues of the intermediary (N) compounds were described in the literature and in particular PCT Application 95/05427.

The invention has as well as its subject matter new industrial products, and notably as new industrial products destined for the production of formula I and II products, the formula I' and M products as is described above.

Certain compounds of the invention may be prepared in the form of pharmaceutically acceptable salts according to the usual methods. The acceptable salts comprise as an example and in a non-limiting manner, the addition salts of inorganic acids such as chlorohydrate, sulfate, phosphate, diphosphate, bromohydrate and nitrate or organic acids such as acetate, maleate, fumarate, tartrate, succinate, citrate, lactate, methane sulfonate, p-toluenesulfonate, pamoate, salicylate, oxalate and stearate. The salts formed from bases such as sodium or potassium hydroxide that enter as well into the field of application of the present invention when they are usable. For other examples of pharmaceutically acceptable salts, refer to "Pharmaceutical Salts", J. Pharm. Sci. 66: 1 (1977).

The compounds of the present invention possess interesting pharmacological properties. This is the way in which the compounds of the present invention have an inhibiting effect on the topoisomerase I and/or II and anti-tumor activity. The present technique suggests that the compounds of the invention present an antiparasitic and/or antiviral activity. The compounds of the present invention may thus be used in different therapeutic applications.

The compounds may inhibit topoisomerase, for example of type I and/or II, in a patient, for example a mammal such as a human, by administration to this patient of an effective therapeutic quantity of a formula (I) or a formula (II) compound.

The compounds of the invention possess as well anti-tumor activity. They may be used for the treatment of tumors, for example tumors expressing a topoisomerase, in a patient by administration to the former of an effective therapeutic quantity of formula (I) or formula (II) compound. Some examples of tumors or cancers comprise cancers of the esophagus, the stomach, the intestines, the rectum, the oral cavity, the pharynx, the larynx, the lungs, the colon, the breast, the uterus cervix, the endometrium corpus, the ovaries, the prostate, the testicles, the bladder, the kidneys, the liver, the pancreas, the bones, the connective tissue, the skin, the eyes, the brain and the central nervous system, as well as cancer of the thyroid, leukemia, Hodgkin's disease, lymphomas other than Hodgkin's, multiple melanomas and others.

They may be used as well for the treatment of parasitic infections by inhibition of the hemoflagellates (for example in trypanosoma or leishmania infections) or by the inhibition of plasmodium (as for example in malaria), but also the treatment of viral infections or illnesses.

These properties make formula I and II products suitable for a pharmaceutical use. The present application has as well as its subject matter, as medications, the formula I and II products as is defined above, as well as the addition salts with the pharmaceutically acceptable organic or mineral acids, said formula I and II products, as well as the pharmaceutical compounds comprising, as an active ingredient, one of the medications as defined above.

The invention concerns thus pharmaceutical compositions comprising a compound of the invention or an additive salt of a pharmaceutically acceptable acid of it, in association with a pharmaceutically acceptable support following the chosen method of administration (for example oral, intravenous, intraperitoneal, intramuscular, transdermal or subcutaneous). The pharmaceutical composition (for example therapeutic) may be in the form of a solid, liquid, liposome or lipid micell.

The pharmaceutical composition may be in the form of solids, for example, powders, pills, granules, tablets, liposomes, capsules or suppositories. The pill, tablet or capsule may be coated in a substance capable of protecting the composition from the action of gastric acid or enzymes in the stomach of the subject during a sufficient period of time to permit the composition to pass, non-digested into the small intestine of the latter. The compound may thus be administered locally, for example by placement next to the tumor. The compound may also be administered according to the time released method (for example a time released composition or an infusion pump). The solid appropriate medium may be, for example, calcium phosphate, magnesium stearate, magnesium carbonate, talc, sugars, lactose, dextrine, amidon, gelatin, cellulose, methyl cellulose, sodium carboxymethyl cellulose, polyvinylpyrolidine, and wax. The pharmaceutical compositions containing a compound of the invention may be presented as well in the form of a liquid like, for example, solutions, emulsions, suspensions or a time-release formulation. The appropriate liquid supports may be, for example, water, organic solvents such as glycerol, or the glycols such as polyethylene glycol, as well as their mixtures, in various proportions, in water.

The invention has as well as its subject matter the use of the formula I and II products as is defined above, for the preparation of medication intended to inhibit topoisomerase, and more particularly type I and type II topoisomerase, of medication intended to treat tumors, of medications intended to treat parasitic infections, as well as medications intended to treat viral infections or illnesses.

The dose of a compound according to the present invention, is anticipated for the treatment of illnesses or disorders mentioned above, vary according to the method of administration, the age and the body weight of the subject under treatment, as well as the condition of the latter, and it will be decided definitively by the treating doctor or veterinarian is called here "therapeutically effective quantity".

In the following experimental section, an illustration of the pharmacological properties of the compounds can be found.

In the case that all the technical and scientific terms used here are not defined in another manner, they have the same significance as the one currently understood by an ordinary specialist in the domain to which the invention pertains. In the same way, all the publications, patent applications, all patents and all other references mentioned here are incorporated by reference.

The following references are presented to illustrate the above procedures and must not in any case be considered as limiting the scope of the invention.

EXPERIMENTAL SECTION

EXAMPLE 1 tert-butyl β-ethyl-β-hydroxy-γ-(8-hydroxymethyl-9-oxo(11H)-indolizino-[1,2-b] quinoline-7-yl)-propionate 1.a. 4-ethyl-3,4-dihydroxy-1H-pyrano [3',4': 6,7] indolizino [1,2-b] quinoline-14 (4H,12H)-one Sodium borohydride (14 g, 370 mmol) is added in portions to a suspension of (S)-(+)-camptothecin (14 g, 40 mmol, that may be obtained using different commercial sources such as Aldrich Chemical Co. (Milwaukee, Wis.)), in methanol (750 ml) and the resulting mixture is heated slowly to 55° C. so as to obtain a clear solution that is then agitated for 16 hours at ambient temperature. The solvent is then evaporated under reduced pressure, the residue is recovered in water (250 ml), neutralized by the addition of acetic acid (21 ml) and left alone for 2 hours at 4° C. The resulting suspension is filtered and washed successively with cold water, acetone and diethyl ether, which, after drying under reduced pressure, permits obtaining the sought compound in the form of a white solid, m.p. 280° C.

1.b. 8-formyloxymethyl-7-propionylindolizino [1,2-b] quinoline-9 (11H)-one

A solution of sodium Metaperiodate (14 g, 65 mmol) in water (140 ml) is added drop-wise to a suspension of 4-ethyl-3,4-dihydroxy-1H-pyrano [3',4': 6,7] indolizino [1,2-b] quinoline-14(4H,12H)-one (13.4 g, 38 mmol) in glacial acetic acid (720 ml) and the resulting solution is agitated for one hour at ambient temperature. The reaction mixture is then poured into a mixture of ice/water (650 ml) and the resulting suspension is agitated for one half-hour then filtered and washed successively with water, isopropyl alcohol, and etherdiethyl alcohol, which, after drying under reduced pressure, the sought compound (11.5 g) in the form of a pale yellow solid, m.p. >200° C. (d).

1.c. tert-butyl β-ethyl-β-hydroxy-γ-(8-hydroxymethyl-9-oxo (11H)-indolizino-[1,2-b] quinoline-7-yl)-propionate A zinc suspension (6.5 g, 100 mmol) agitated with a magnetic agitator in anhydrous diethylether (50 ml) under argon, is activated, by drop-wise addition of chlorotrimethylsilane (0.75 ml, 5.7 mmol). Agitate again 15 minutes at ambient temperature to heat to reflux. The heating bath is then removed and tert-butyl bromoacetate (15 ml, 100 mmol) is added drop-wise at a rate assuring the maintenance of reflux. The external heating is replaced and pursued again for one hour. The ethered solution resulting from the Reformatsky reagent is left to cool to ambient temperature then transferred, by means of a cannula, into a suspension of 8-formyloxymethyl-7-propionylindolizino [1,2-b] quinoline-9 (11H)-one (1.6 g, 4.7 mmol) in anhydrous tetrahydrofuran (40 ml) under argon. The reaction mixture is agitated at reflux for one hour, then left to cool to ambient temperature, and the reaction is stopped by adding saturated ammonium chloride (100 ml) and is extracted with chloroform (3×100 ml). The combined chloroformic extracts are dried on sodium sulfate, evaporated, and the residue is purified by gel chromatography on silica gel (1–2% MEOH/ $CH_2Cl_2$), which makes possible obtaining 0.64 g of the sought-after compound (31%) in the form of a pale yellow solid, m.p. 146–149° C.

NMR-¹H (CDCl₃); 0.93 (t, 3H); 1.37 (s, 9H); 1.99 (m, 2H); 2.97 (dd, 2H); 3.5 (se, 1H); 5.10 (s, 2H); 5.24 (s, 2H); 7.40 (s, 1H); 7.59 (t, 1H); 7.83 (t, 1H); 7.90 (d, 1H); 8.20 (d, 1H); 8.34 (s, 1H).

NMR-C¹³ (CDCl₃); 8.18; 27.90; 34.59; 45.34; 49.91; 58.55; 77.39; 82.42; 100.52; 127.67; 127.97; 128.10; 128.64; 129.44; 129.79; 130.42; 130.99; 142.86; 148.69; 152.75; 155.16; 162.38; 172.24.

IR (KBr); 764; 1016; 1157; 1580; 1651; 1726.

EXAMPLE 2 ethyl β-ethyl-β-hydroxy-γ-(8-hydroxymethyl-9 oxo (11H-indolizino-[1,2-b] quinoline-7-yl)-propionate A suspension of zinc (500 mg, 7.64 mmol) and of 8-formyloxymethyl-7-propionylindolizino [1,2-b] quinoline-9 (11H)-one (400 mg, 1.15 mmol) in anhydrous tetrahydrofuran (20 ml) containing 10 mg of hydroquinone is heated to reflux under argon. The heating bath is removed and the exothermic reaction initiated by the addition of a drop of ethyl bromoacetate and a small crystal of iodine. Reflux is maintained by the drop-wise addition of ethyl bromoacetate (500 ml, 4.48 mmol) then the reaction mixture is again heated at reflux for one hour. After cooling to ambient temperature, the reaction is stopped by adding saturated ammonium chloride (10 ml) and methanol (30 ml). The resultant mixture is agitated for 5 minutes then filtered and evaporated. The residue is dissolved in dichloromethane (30 ml), washed with water and dried on sodium sulfate. This is followed by the elimination of the solvent and a purification by column chromatography (SiO₂, CH₂Cl₂/MeOH 98/2) resulting in 230 mg (49%) of the sought compound in the form of a yellow solid, m.p. 157–161° C.

NMR ¹H (CDCl₃): 0.93 (t, 3H); 1.20 (t, 3H); 2.02 (m, 2H); 3.07 (dd, 2H); 4.11(q, 2H); 4.9 (se, 1H); 5.08 (s, 2H); 5.23 (s, 2H); 7.45 (s, 1H); 7.62 (t, 1H); 7.80 (t, 1H); 7.90 (d, 1H); 8.22 (d, 1H); 8.36 (s, 1H).

NMR C¹³ (CDCl₃): 8.09; 14.01; 34.67; 44.85; 49.94; 58.31; 61.09; 77.21; 100.78; 127.78; 127.96; 128.11; 128.72; 129.16; 129.65; 130.60; 131.32; 142.76; 148.28; 152.55; 155.09; 162.22; 172.59.

IR (KBr): 766; 1009; 1184; 1582; 1647; 1750.

EXAMPLE 3

5-ethyl-4,5-dihydro-5-hydroxy-1H-oxepino [3',4': 6, 7]-indolizine [1,2-b]quinoline-3,15 (4H, 13H)-dione tert-butyl β-ethyl-β-hydroxy-γ-(8-hydroxymethyl-9-oxo (11H)-indolizino-[1,2-b] quinoline-7-yl) propionate (1.45 g, 3.32 mmol) is dissolved in anhydrous dichloromethane (25 ml) and treated with a saturated solution of hydrogen chloride in dichloromethane (100 ml). The resultant mixture is maintained at −20° C. for 16 hours. The precipitate is filtered, washed with methanol and dried under reduced pressure, which obtains 662 mg (55%) of the sought compound in the form of a yellow solid, m.p. >300° C.

NMR ¹H (DMSO): 0.90 (t, 3H); 1.20 (q, 2H); 3.27 (dd, 2H); 5.29 (s, 2H); 5.49 (dd, 2H); 7.42 (s, 1H); 7.73 (t, 1H); 7.90 (t, 1H); 8.16 (t, 2H); 8.71 (s, 1H).

NMR C¹³ (DMSO): 8.45; 36.48; 42.54; 50.68; 61.44; 73.34; 99.78; 122.71; 127.83; 128.15; 128.75; 129.08; 130.07; 130.61; 131.81; 144.66; 148.04; 152.80; 155.91; 159.26; 172.08.

IR (KBr): 761; 1127; 1204; 1285; 1580; 1653; 1757.

EXAMPLE 4

β-ethyl-β-hydroxy-γ-(8-hydroxymethyl-9-oxo (11H)-indolizino-[1,2-b] quinoline-7-yl)-propionic acid An aqueous solution of potassium hydroxide (0.1N, 30 ml) is added to 5-ethyl-4,5-dihydro-5-hydroxy-1H-oxepino [3'4': 6,7]-indolizino [1,2-b] quinoline-3,15 (4H, 13H)-dione (500 mg, 1.38 mmol) and the resultant suspension is agitated for 16 hours, which results in an almost clear liquid that is filtered. The filtrate is acidified to pH 3.5 with 1N hydrochloric acid, and the yellow precipitate is recovered by filtration, washed with water and acetone, then dried under reduced pressure. 415 mg (79%) of the sought compound is obtained in the form of a monohydrate, m.p. 165–167° C.

NMR ¹H (DMSO): 0.82 (t, 3H); 2.10 (m, 2H); 2.83 (d, 2H); 3.12 (d, 2H); 3.25 (se, 1H); 4.81 (s,2H); 5.26 (s,2H); 5.76 (se, 1H); 7.38 (s, 1H); 7.71 (t, 1H); 7.84 (t, 1H); 8.10 (d, 1H); 8.18 (d, 1H); 8.34 (s, 1H); 12.15 (se, 1H).

NMR C¹³ (DMSO): 8.16; 34.80; 46.71; 50.36; 55.73; 76.53; 100.17; 127.50; 128.00; 128.26; 128.69; 129.06; 130.01; 130.45; 131.63; 142.57; 148.09; 153.19; 156.07; 161.22; 172.27.

IR (KBr): 1020; 1188; 1413; 1586; 1651; 1694.

EXAMPLE 5 methyl β-ethyl-β-hydroxy-γ-(8-hydroxymethyl-9-oxo (11H)-indolizino-[1,2-b] quinoline-7-yl)-propionate 5-ethyl-4,5-dihydro-5-hydroxy-1H-oxepino [3'4': 6,7]-indolizino [1,2-b] quinoline-3,15 (4H,13H)-dione (180 mg, 0.5 mmol), in suspension in methanol (50 ml) is treated with 6N dry hydrogen chloride in methanol (0.5 ml) and maintained at reflux until completely dissolved (4 hours). The volatile compounds are evaporated and the residue is dissolved in dichloromethane (50 ml), washed with diluted sodium hydroxide (0,05N, 15 ml) and saline (15 ml). The organic fraction is dried on sodium sulfate and evaporated. The residual solid is purified by silica gel column chromatography (MeOH at 3% / CH2Cl2) and the product is purified and recovered in diethyl ether, filtered and dried, which gives 120 mg (58%) of the sought after compound in the form of a pale yellow solid, m.p. 163–166° C.

NMR ¹H (CDCl₃): 0.93 (t, 3H); 2.2 (m, 2H); 3.05 (dd, 2H); 3.49 (s, 3H); 3,62 (s, 3H); 4.93 (s, 2H); 5.22 (d, 2H); 5.52 (s, 1H); 7.21 (s, 1H); 7,62 (t, 1H); 7.81(t, 1H); 7.91 (d, 1H); 8.22 (d, 1H); 8.36 (s, 1H).

NMR C¹³ (CDCl₃): 7.74; 35.54; 46.82; 50.15; 51.67; 58.10; 65.33; 78.03; 100.17; 125.57; 127.70; 128.04; 128.10; 128.35; 129.53; 130.39; 130.94; 143.87; 148.75; 152.94; 157.83; 161.74; 171.35.

IR (KBr): 1207; 1595; 2655; 1709.

EXAMPLE 6 ethyl β-ethyl-α,α-difluoro-β-hydroxy-γ-(8-hydroxymethyl-9-oxo (11H)-indolizino-[1,2-b] quinoline-7-yl)-propionate About one half of the total quantity of ethyl bromodifluoroacetate (1.8 ml, 14 mmol), 8-formyloxymethyl-7-propionylindolizino [1,2-b] quinoline-9 (11H)-one (2.0 g, 5.75 mmol) such as is obtained in example 1.b.) in suspension with anhydrous THF (10 ml), is added drop-wise under argon to a suspension of zinc (1.25 g, 17.2 mmol) in anhydrous THF at reflux (40 ml), then the remaining part of the ethyl bromodifluoroacetate [is added]. The reaction mixture is maintained at reflux for another half-hour. After cooling to ambient temperature, the reaction is stopped by adding saturated aqueous ammonium chloride (20 ml) and the reaction mixture is extracted with dichloromethane (3×20 ml). The combined organic extracts are dried and concentrated. The residue is recovered in diethyl ether (10 ml), filtered and purified by column chromatography (SiO$_2$, CH$_2$Cl$_2$/MeOH 98/2), resulting in 664 mg (26%) of the sought compound in the form of a yellow solid, m.p. 208–209° C.

NMR $^1$H (CDCl$_3$): 0.91(t, 3H); 1.38 (t, 3H); 2.32 (m, 2H); 4.8 (se, 1H); 4.38 (q. 2H); 5.09 (d, 2H); 5.13 (dd, 2H); 7.42 (s,1H); 7.55 (t, 1H); 7.72 (t, 1H); 7.79 (d, 1H); 8.08 (d, 1H); 8.22 (s, 1H).

NMR C$^{13}$ (CDCl$_3$): 6.97; 13.93; 28.63; 50.18; 56.27; 63.15; 77.20; 81.96 (t); 101.27; 116.40 (t); 127.67; 127.77; 127.97; 128.31; 129.26; 130.33; 130.94; 131.23; 143.16; 148.34; 150.20; 151.91; 161.21; 163.21 (t).

IR (KBr): 1124; 1308; 1591; 1647; 1748.

EXAMPLE 7 ethyl β-ethyl-β-hydroxy-γ-(8-hydroxymethyl-9-oxo (11H)-indolizino-[1,2-b] quinoline-7-yl)-propionate A suspension of zinc (1.25 g, 19.1 mmol) of 8-methyl-7-propionylindolizino [1,2-b] quinoline-9-(11H)-one (500 mg, 1.43 mmol, such as is obtained by Kingsbury, W. D., Tetrahedron Lett. 29: 6847 (1988)) and silver acetate (250 mg, 1.50 mmol) in tetrahydrofuran (10 ml) is agitated at ambient temperature in an argon atmosphere. At the end of 10 minutes, the reaction mixture is activated by the drop-wise addition of a molar solution of chlorodiethylaluminum (10 ml, 10 mmol), then ethyl bromoacetate (1.25 ml, 11.3 mmol) is added drop-wise and the resultant mixture is left to react for another 5 hours. The reaction is stopped by the successive addition of ethyl alcohol (10 ml) and a saturated solution of potassium and sodium tartrate (10 ml). The resultant mixture is agitated again for one hour, filtered and concentrated under reduced pressure. The residue is recovered in dichloromethane (30 ml), washed with water, dried, concentrated and purified by column chromatography (SiO$_2$, CH$_2$Cl$_2$/MeOH 98/2), resulting in 93 mg (15%) of the sought product in the form of a pale yellow solid, m.p. 185–188° C.

NMR $^1$H (CDCl$_3$): 0.91 (t, 3H); 1.17 (t, 3H); 1.99 (m, 2H); 2.49 (s, 3H); 3.10 (dd, 2H); 4.11 (q, 2H); 4.6 (se, 1H) 5.25 (s, 2H); 7.65 (t, 1H); 7.67 (s,1H); 7.80 (t, 1H); 7.90 (d, 1H); 8.22 (d, 1H); 8.34 (s, 1H).

NMR C$^{13}$ (CDCl$_3$): 8.02; 13.99; 14.72; 33.14; 43.97; 50.02; 61.0; 76.54; 101.90; 127.65; 127.84; 128.08; 128.81; 128.88; 130.74; 131.59; 131.65; 140.33; 147.64; 152.96; 153.61; 162.11; 172.91.

IR (KBr): 762; 1192; 1576; 1653; 1740.

EXAMPLE 8 tert-butyl β-ethyl-β-hydroxy-γ-(8-hydroxymethyl-9-oxo (11H)-indolizino-[1,2-b] quinoline-7-yl)-propionate Acetic anhydride (70 μl, 0.7 mmol) is added dropwise to a solution of tert-butyl β-ethyl-β-hydroxy-γ-(8-hydroxyinethyl-9-oxo (11H)-indolizino-[1,2-b] quinoline-7-yl)-propionate (200 mg, 0.46 mmol) and triethylamine (140 μl, 1 mmol) in dichloromethane (5 ml) and the resultant mixture is agitated at ambient temperature for 21 hours. The volatile compounds are evaporated and the residue is purified by a silica gel column chromatography (1–2% MeOH/CH$_2$Cl$_2$), resulting in 152 mg of the sought compound in the form of a yellow solid, m.p. 195–196° C.

NMR $^1$H (CDCl$_3$): 0.88 (t, 3H); 1.32 (s, 9H); 1.93 (m, 2H); 2.07 (s, 3H); 2.97 (dd, 2H); 4.8 (se, 1H); 5.28 (s, 2H); 5.59 (dd, 2H); 7.39 (s, 1H); 7.63 (t, 1H); 7.80 (t, 1H); 7.90 (d, 1H); 8.23 (d, 1H); 8.34 (s, 1H).

NMR C$^{13}$ (CDCl$_3$): 8.02; 21.06; 27.91; 35.05; 45.58; 50.16; 59.23; 77.52; 82.26; 100.59; 124.21; 127.91; 128.10; 128.14; 128.97; 129.18; 130.68; 131.46; 142.85; 148.29; 152.43; 158.49; 161.83; 171.13; 171.90.

EXAMPLE 9

5,12-diethyl-4,5-dihydro-5-hydroxy-1H-oxepino [3', 4': 6,7]-indolizino [1,2-b] quinoline-3,15 (4H,13H)-dione This compound is prepared in a manner analogous to example 1, except that in stage 1.a. the 7-ethyl camptothecin (Sawada et al., Chem. Pharm. Bull. 39: 2574 (1991)) is used in place of the camptothecin. The sought compound is obtained in the form of a bright yellow solid, m.p. >270° C.

NMR $^1$H (DMSO): 0.92 (t, 3H); 1.39 (t, 3H); 1.93 (q, 2H); 3.08 (d, 2H); 3.25 (q, 2H); 3.51 (d, 2H); 5.32 (s, 2H); 5.52 (dd, 2H); 7.42 (s, 1H); 7.76 (t, 1H); 7.89 (t, 1H); 8.18 (d, 1H); 8.32 (d, 1H).

NMR C$^{13}$ (DMSO): 8.46; 14.15; 22.42; 36.50; 42.54; 49.95; 61.45; 73.35; 99.68; 122.61; 124.27; 126.76; 127.70; 128.27; 129.92; 130.18; 145.17; 145.82; 148.57; 152.15; 155.89; 159.26; 172.08.

EXAMPLE 10

β-ethyl-γ-(12-ethyl-8-hydroxymethyl-9-oxo (11H)-indolizino-[1,2-b] quinoline-7-yl)-β-hydroxy-propionic acid This compound is prepared in a manner analogous to example 4, except that 5,12-diethyl-4,5-dihydro-5-hydroxy-1H-oxepino [3'4': 6,7]-indolizino [1,2-b] quinoline-3,15 (4H,13H)-dione is used in place of 5-ethyl-4,5-dihydro-5-hydroxy-1H-oxepino [3'4': 6,7]-indolizino [1,2-b] quinoline-3,15 (4H,13H)-dione. It is obtained in the form of a slightly off-white solid, m.p. 238–239° C.

NMR $^1$H (DMSO): 0.82 (t, 3H); 1.35 (t, 3H); 2.01 (m, 2H); 2.85 (d, 2H); 3.18 (d, 2H); 3.22 (q, 2H); 4.81 (s, 2H); 5.00 (se, 1H); 5.24 (s, 2H); 5.78 (se, 1H); 7.38 (s, 1H); 7.77 (t, 1H); 7.86 (t, 1H); 8.18 (d, 1H); 8.28 (d, 1H); 12.10 (se, 1H).

NMR C$^{13}$ (DMSO): 8.12; 14.15; 22.41; 34.78; 46.74; 49.65; 55.71; 76.51; 100.04; 124.22; 126.63; 127.48; 128.12; 128.21; 129.94; 130.02; 143.10; 145.59; 148.69; 152.62; 156.03; 161.22; 172.22.

EXAMPLE 11

8-ethyl-2,3,8,9-tetrahydro-8-hydroxy-10H-[1,4] dioxino [2,3-g] oxepino[3',4':6,7] indolizino [1,2-b] quinoline-10,13 (15H)-dione 11.a. 2-ethyl-2-(2-methoxy-4-pyridyl)-1,3dioxolane (F)

Azeotropic water is distilled for one entire night with a Dean Stark apparatus from a mixture of 2-chloro-4-propionylpyridine (10 g, 59 mmol) obtained as in Lamattina, J. L., J. Heterocyclic Chem. 20, p. 553 (1983)), of ethylene glycol, and of p-toluenesulfolic acid 250 mg) in toluene 150 ml). The solvent is then eliminated under reduced pressure, the acid is neutralized with saturated aqueous sodium bicarbonate (100 ml) and the product is extracted using ether. The combined ethered extracts are washed with saline, dried on sodium sulfate and evaporated, which produces 13.3 g (96%) of the crude product protected by the carbonyl group which is brought to reflux with 3 equivalents of sodium methoxide in acetonitrile until the end of the reaction (control by thin bed chromatography: $SiO_2$, tert-butyl methyl oxide / hexane (TBMO/HX) 50/50). The acetonitrile solution is then filtered and evaporated. The residue is recovered in ether, washed with water and saline, dried on sodium sulfate and evaporated, resulting in a brown oil which is distilled (70–75° C, 0.04 mbar); 10.7 g (global return 81%) of product (F) is recovered in the form of a clear liquid.

11.b. 2-ethyl-2-(3-hydroxymethyl-2-methoxy-4-pyridyl)-1,3-dioxolane (G)

Tert-butyllithium (1.7 M in pentane, 100 ml, 170 mmol) is added drop-wise using a cannula to a solution of bromomesitylene (13 ml, 85 mmol) in anhydrous tetrahydrofurane (300 ml) at −78° C. under argon. The resultant white precipitate is agitated at −78° C. for one hour then 2-ethyl-2-(2-methoxy-4-pyridyl)-1,3-dioxolane (10 g, 44.8 mmol) is added and the reaction mixture is agitated 15 minutes at −78° C., one hour at 0° C. and one hour at ambient temperature. After another cooling to −78° C., anhydrous N,N-dimethylformamide (100 mmol) is added and the reaction mixture is left to reheat to ambient temperature then is agitated for 16 hours, after which there is an analysis by thin bed chromatography ($SiO_2$, TBMO/HX: 50/50) makes the complete consumption of the starting compound. The reaction is stopped with saturated ammonium chloride and the reaction mixture is extracted with diethyl ether (200 ml, 50 ml, 50 ml). The combined extracts are dried on sodium sulfate and evaporated, resulting in a yellow oil which is purified by column chromatography ($SiO_2$, TBMO/HX: 0/100 to 5/95 in order to elute the mesytylene derivatives then 20/80 to 50/50 to elute the product) resulting in the intermediary aldehyde (7 g). The aldehyde is dissolved in methanol (100 ml) and treated with sodium borohydride (5 g, 132 mmol) and the resultant mixture is agitated until the complete consumption of the intermediary aldehyde (about 1 hour) by analytic determination by thin bed chromatography. The solvent is then evaporated, the residue is recovered in ether, washed with water and saline, dried, and the solvent is evaporated. The column chromatography ($SiO_2$, TBMO/HX: 10/90 to 50/50) of the residue gives 7 g (global return 62%) of product (G) in the form of a yellow oil.

11.c. 2-(3-benzyloxymethyl-2-methoxy-4-pyridyl)-2-ethyl-1,3-diocolane (H)

A solution of 2-ethyl-2-(3-hydroxymethyl-2-methoxy-4-pyridyl)-1,3-dioxolane (7 g, 30 mmol) and of benzyl chloride (5 ml, 45 mmol) in anhydrous tetrahydrofuran (150 ml) is added drop-wise to a suspension of sodium hydride (80% in mineral oil, 1.85 g, 61 mmol) in anhydrous tetrahydrofuran (100 ml) and the reaction mixture is maintained at reflux for 16 hours. The reaction mixture is then left to cool to ambient temperature, the reaction is stopped with water (50 ml) and the reaction mixture is concentrated under reduced pressure. The residue is dissolved in diethyl ether (150 ml) and washed with water and saline, dried and evaporated. A purification by column chromatography ($SiO_2$, TBMO/HX; 5/95 to 20/80) results in the product protected by the benzyl (H). 9 g. (87%) in the form of a clear oil.

11.d. 1-(3-benzyloxymethyl-2-methoxy-4-pyridyl)-propane-1-one (I')

2-(3-benzyloxymethyl-2-methoxy4-pyridyl)-2-ethyl-1,3-dioxolane (9 g, 27 mmol) is treated with trifluoracetic acid (10 ml) and water (5 ml) in a temperature bath of 120° C. for 3 hours. The reaction mixture is concentrated under reduced pressure and the residual traces of the acids are neutralized by the addition of a saturated aqueous sodium bicarbonate. An ether extraction is followed by column chromatography ($SiO_2$, TBMO/HX; 10/90) results in 5.5 g (70%) of product (I).

11.e. tert-butyl β-ethyl- β-hydroxy-γ-(3-benzyloxymethyl-2-methoxy-4pyridyl) propionate Tert-butyl bromoacetate (13 ml, 80 mmol) is added drop-wise to a suspension of zinc (5.3 g, 80 mmol activated by treatment with 6N HCl for 10 seconds, then washed successively with water until neutral pH, acetone and diethyl ether) in anhydrous tetrahydrofuran (60 ml) to reflux. The reaction medium is maintained at reflux for another 10 minutes after which the addition is finished. The a solution of 1-(3-benzyloxymethyl-2-methoxy-4-pyridyl)propane-1-one (5.8 g, 20 mmol) in anhydrous tetrahydrofuran (20 ml) is added, and the reaction mixture is agitated under reflux for one more hour. The reaction is stopped at 0° C. with saturated aqueous ammonium chloride (100 ml) and the reaction mixture extracted with diethyl ether. The combined extracts are dried on sodium sulfate and evaporated, resulting in a yellow oil which is purified by column chromatography ($SiO_2$, TBMO/HX: 5/95 to 10/90) to obtain the tert-butyl ester (j)(7 g 8 95%) in the form of a clear oil.

11.f. tert-butyl β-ethyl-β-hydroxy-γ-(3-hydroxymethyl-2-methoxy-4-pyridyl) propionate Tert-butyl β-ethyl-β-hydroxy-γ-(3-hydroxymethyl-2-methoxy-4-pyridyl) propionate (1 g, 2.5 mmol) is hydrogenolised at atmospheric pressure and ambient temperature by using 5% of palladium on charcoal as a catalyst (50 mg) and absolute ethanol as solvent (10 ml). Once the reaction is finished (6 hours), the catalyst is separated by filtration and the solvent is evaporated, which yields 0.7 g (90%) of product (K) of a sufficient purity for a subsequent synthetic use.

11.g. 5-ethyl-1,5-dihydro-5-hydroxy-9-methoxy-oxepino [3,4-c] pyridine-3 (4H)-one (L)

Tert-butyl β-ethyl-β-hydroxy-γ-(3-hydroxymethyl-2-methoxy-4-pyridyl) propionate (8.8 g, 28 mmol) is treated with trifluoroacetic acid (30 ml) for 3 hours at ambient temperature. The volatile components are evaporated and the residue is purified by column chromatography ($SiO_2$, $CH_2Cl_2$/MeOH: 100/0 to 98/2), which results in a clear oil, after treatment with toluene, gives 5.9 g of product (L) (89%) in the form of white crystals, m.p. 97–98° C.

11.h. 5-ethyl-1,5-dihydro-5-hydroxy-oxepion [3,4-c] pyridine 3,9(4H,8H)dione (M)

Hydrochloric acid 1N (20 ml), 5-ethyl-1,5-dihydro-5-hydroxy-9-methoxy-oxepino [3,4-c] pyridine-3 (4H)-one (0.5 g, 2.1 mmol) is heated to reflux for 9 hours. The reaction mixture is concentrated under pressure and the residue is again dried by the addition and evaporation of toluene, two times, then left overnight under reduced pressure in the presence of phosphorous pentoxide. The resultant oil is dissolved in anhydrous acetonitrile (5 ml) and agitated under argon for 24 hours. The precipitate is filtered and dried, which yields 0.23 g (49%) of a white solid (M), m.p. 118–119° C.

11.i. 6,7-ethylenedioxy-2-iodo-3-quinoline-methanol (N)

The procedures described by Meth-Cohn et al; J. Chem. Soc. Perkin Trans. I, p. 1520 (1981); Meth-Cohn, J. Chem.

Soc. Perkin Trans. I, p. 2509 (1981), and Nakasimhan et al, J. Am. Chem. Soc. 112, p. 4431 (1990), are used. 3,4-ethylenedioxyacetanilide (22 g, 113 mmol) is added to the Vilsmeyer reagent obtained by the drop-wise addition of phosphoryl oxychloride (71 ml, 0.77 mol) to anhydrous dimethylformamide (23 ml, 0.28mol), chilled in an ice-water bath for another 0.5 hour in an argon atmosphere. The resultant mixture is heated to 75° C. for 16 hours. After cooling to ambient temperature, the reaction mixture is added to a mixture of ice and water (300 ml) and extracted with dichloromethane (5×200 ml). The combined organic extracts are dried on sodium sulfate, filtered and concentrated. The solid residue is placed into suspension in dichloromethane (20 ml), filtered and dried under reduced pressure, which results in 10 g (35%) of 2-chloro-6,7-ethylenedioxyquinoline-3-carbaldehyde in the form of a yellow solid, m.p. 222–224° C. This intermediary is treated with sodium iodide (30 g, 0.2 mol) and concentrated hydrochloric acid (1.5 ml) in acetonitrile to reflux (150 ml) for 24 hours. After cooling to ambient temperature, the solvent is eliminated under reduce pressure and the residue is recovered in 50% aqueous tetrahydrofuran (200 ml), filtered, washed with tetrahydrofuran and dried under reduced pressure, which yields 12 g of 6,7-ethylenedioxy-2-iodoquinoline-3-carbaldehyde in the form of a yellow solid, m.p. 155–157° C. The above intermediary is treated with sodium borohydride (2 g, 52 mmol) in methanol (200 ml) at ambient temperature for 0.5 hours. The solvent is eliminated under reduced pressure and the residue is recovered in water and filtered. The resultant solid is dried under reduced pressure in the presence of phosphorous pentoxide, resulting in 11 g of (6,7-ethylenedioxy-2-iodoquinoline-3-yl)-methanol in the form of a yellow solid, m.p. 178–180° C.

11.j. 5-ethyl-8-(6,7-ethylenedioxy-2-iodo-3-quinolinemethyl)-1,5-dihydro-5-hydroxy-oxepino [3,4-c] pyridine 3,9(4H,8H)-dione (O)

Over 5 minutes, diethyl azodicarboxylate (570 µl, 3.6 mmol) is added drop-wise to a solution of 5-ethyl-1, 5dihydro-5-hydroxy-oxepino [3,4-c] pyridine 3,9(4H,8H)-dione (400 mg, 179 mmol), of compound obtained in the preceding stage 11.i. (770 mg, 2.23 mmol) and triphenylphosphine (934 mg, 3.58 mmol) in a mixture of anhydrous THF/DMSO (8/1 v/v, 45 ml) and the resultant mixture is agitated under argon at ambient temperature for 16 hours. The reaction mixture is then concentrated under reduced pressure and the residue is dissolved in chloroform (100 ml). The resultant solution is washed with saline (4×50 ml), dried on sodium sulfate and evaporated. The residue is purified by column chromatography (SiO$_2$, CH$_2$Cl$_2$/ MEOH: 99/1 to 98/2), resulting in 650 mg (66%) of product (O) in the form of a white solid, m.p. 165–167° C.

11.k. 8-ethyl-2,3,8,9-tetrahydro-8-hydroxy-10H, 12H-[1,4] dioxino [2,3-g] oxepino [3',4':6,7] indolizino [1,2-b] quinoline-10,13 (15H )-dione 5-ethyl-8-(6,7-ethylenedioxy-2-iodoquinoline-3-yl) methyl-4,5-dihydro-5-hydroxy-(1H,3H)oxepino [3,4-c] pyridine-3-dione (600 mg, 1.1 mmol), tetrabutyl-ammonium bromide (352 mg, 1.1 mmol), sodium acetate (359 mg, 4.4 mmol) and palladium II acetate (98 mg, 0.43 mmol) are dissolved in anhydrous acetonitrile (40 ml) and heated to 90° C. under argon for 16 hours. After cooling to ambient temperature, a white precipitate is separated from the reddish solution. This precipitate is filtered and dried under reduced pressure. The crude product is put into suspension in water, filtered and dried under reduced pressure on phosphorous pentoxide, resulting in 250 mg of the sought compound in the form of a clear yellow solid, m.p. >250° C.

NMR-$^1$H (DMSO): 0.91 (t, 3H); 1.87 (m, 2H); 3.08 (d, 1H); 3.51 (d, 1H); 4.45 (s, 2H); 5.19 (s, 2H); 5.47 (dd, 2H); 6.02 (se, 1H); 7.33 (s, 1H); 7.54 (s, 1H); 7.55 (s, 1H); 8.43 (s, 1H).

NMR-C$^{13}$ (DMSO): 8.43; 36.47; 42.54; 50.52; 61.43; 64.43 (2C); 73.31; 99.07; 112.27; 113.14; 122.00; 124.24; 128.18; 129.74; 144.59; 145.01; 145.33; 147.63; 150.88; 155.88; 159.23; 172.07.

EXAMPLE 12

10-benzyloxy-5-ethyl-4,5-dihydro-5-hydroxy-1H-oxepino [3',4':6,7]-indolizino [1,2-b] quinoline-3,15 (4H,13H)-dione 12.a. (6-benzyloxy-2-iodo-3-quinoline)-methanol This compound is prepared in a method analagous to that outlined in stage 11.i. of example 11, but in using 4-benzyloxyacetanilide in place of 3,4-ethylenedioxyacetanilide. A purification by column chromatography on silica gel and the use of dichloromethane as eluant are necessary to isolate (8% return) to a sufficient purity the intermediary 6-benzyloxy-2-chloroquinoline-3-carbaldehyde, m.p. 180–182° C. Next, the exchange of the subsequent halogen reduction to sodium borohydride results in (6-benzyloxy-2-iodoquinoline-3-yl)-methanol, m.p. 147–149° C.

12.b. 8-(6-benzyloxy-2-iodo-3-quinolinemethyl)-1, 5-dihydro-5-ethyl-5-hydroxy-oxepino[3,4-c] pyridine-3,9(4H,8H)-dione This compound is prepared in a method analagous to that outlined in stage 11.j. of example 11, but using (6-benzyloxy-2-iodoquinoline-3-yl)-methanol in place of 6,7-ethylenedioxy-2-iodoquinoline-3-yl)-methanol. This compound appears in the form of a white solid, m.p. 197–199° C.

12.c. 10-benzyloxy-5-ethyl-4,5-dihydro-5-hydroxy-1H-oxepino [3',4':6,7]-indolizino [1,2-b] quinoline-3,15 (4H,13H)-dione This compound is prepared in a method analagous to the one indicated in stage 11.k. of example 11, but using 8-(6-benzyloxy-2-iodo-3-quinolinemethy)-1,5-dihydroxy-5-ethyl-5-hydroxy-oxepino [3,4-c] pyridine-3,9(4H,8H)-dione in place of 5-ethyl-8-(6,7-ethylenedioxy-2-iodoquinoline-3-yl)methyl-4,5-dihydro-5-hydroxy-(1H,3H) oxepino [3,4-c] pyridine-3-dione. The sought compound appears in the form of a clear yellow solid, m.p. >250° C.

NMR-$^1$H (DMSO): 0.90 (t, 3H); 1.85 (m, 2H); 3.08 (d, 1H); 3.50 (d, 1H); 5.25 (s, 2H); 5.30 (s, 2H); 5.50 (dd, 2H); 6.05 (s, 1H); 7.30–7.70 (m, 8H); 8.10 (d, 1H); 8.55 (s, 1H).

NMR-C$^{13}$ (DMSO): 8.43; 36.48; 38.28; 50.65; 61.42; 70.00; 73.32; 99.05; 107.71; 122.05; 123.42; 128.18; 128.26; 128.70; 129.40; 130.19; 130.48; 130.63; 136.65; 144.18; 144.90; 150.53; 155.91; 157.31; 159.24; 172.06.

EXAMPLE 13

γ-(12-benzyloxy-8-hydroxymethyl-9-oxo (11H)-indolizino [1,2-b] quinoline-7-yl)-β-ethyl-β-hydroxy-propionic acid (E)

This compound is prepared in a manner analagous to the one explained in example 4, but using 10-benzyloxy-5- ethyl-4,5-dihydro-5-hydroxy-1H-oxepino [3',4':6,7]-indolizino [1,2-b]quiolline-3,15 (4H,13H)-dione in place of 5-ethyl-4,5-dihydro-5-hydroxy-1H-oxepino [3',4':6,7]-indolizino [1,2-b] quinoline-3,15 (4H,13H)-dione. It appears in the form of a yellow solid, m.p. 171–173° C.

NMR-$^1$H (DMSO): 0.80 (t, 3H); 2.00(m, 2H); 2.85 (d, 1H); 3.15(d, 1H); 4.80 (s, 2H); 5.25 (s, 2H); 5.30 (s, 2H); 5.75 (se, 1H); 7.30 (s, 1H); 7.35–7.70 (m, 7H); 8.10 (d, 1H); 8.55 (s, 1H).

NMR-C$^{13}$ (DMSO): 8.11; 34.75; 46.68; 50.35; 55.70; 69.97; 76.51; 99.45; 107.78; 123.28; 127.64; 128.18 (2C); 128.26; 128.70 (2C); 129.33; 130.17; 130.47; 130.57; 136.69; 142.79; 144.17; 150.93; 156.03; 157.19; 161.20.

EXAMPLE 14

5-ethyl-4,5-dihydro-5,10,-dihydroxy-1H-oxepino [3',4':6,7]-indolizino [1,2-b] quinoline-3,15 (4H, 13H)-dione 10-benzyloxy-5-ethyl-4,5-dihydro-5-hydroxy-1H-oxepino [3',4':6,7]-indolizino [1,2-b] quiolline-3,15 (4H, 13HO-dione (370 mg, 0.79 mmol) is treated with hydrogen at atmospheric pressure and at ambient temperature by using 10% palladium on charcoal as catalyst (60 mg) and trifluoroacetic acid as solvent (15 ml). Once the reaction is terminated (16 hours), dichloromethate (50 ml) and methanol (50 ml) are added to the reaction mixture, the catalyst is filtered and the volatile components are evaporated under reduced pressure, which permits obtaining the crude form of the sought compound containing traces of trifluoroacetic acid. These traces are eliminated by codistillation with 1,4-dioxane. The product obtained is in the form of an orange solid, m.p. 150° C. (d), with a purity sufficient for any further synthetic use.

NMR-$^1$H (DMSO) 0.89 (t,3H); 1.85(q, 2H); 3.02 (d, 1H); 3.45 (d, 1H); 5.19 (s, 2H); 5.37 (d, 1H); 5.50 (d, 1H); 5.98 (se, 1H); 7.26 (s, 1H); 7.31 (s, 1H); 7.40 (d, 1H); 8.00 (d, 1H); 8.42 (s, 1H); 10.32 (s, 1H).

NMR-C$^{13}$ (DMSO): 8.47; 36.50; 42.61; 50.57; 61.46; 73.35; 98.84; 109.02; 121.83; 123.18; 129.50; 129.85; 130.12; 130.80; 143.39; 145.10; 149.69; 155.97; 156.82; 159.30; 172.11.

EXAMPLE 15

11-(dimethylamino)methyl-5-ethyl-4,5-dihydro-5, 10-dihydroxy-1H-oxepino [3',4':6,7]-indolizino [1,2-b] quinoline-3,15 (4H,13H)-dione 15.a. 11 -(dimethylarnino)methyl-5-ethyl-4,5-dihydro-5,10-dihydroxy-1H-oxepino [3',4':6,7]-indolizino [1,2-b] quinoline-3,15 (4H,13H)-dione A suspension of 10-benzyloxy-5-ethyl-4,5-dihydro-5-hydroxy-1H-oxepino [3',4':6,7]-indolizino [1,2-b] quioline-3,15 (4H,13H)-dione (260 mg, 0.69 mmol) in acetic acid (15 ml) is treated with 37% aqueous formaldehyde (500 µl) and 40% aqueous dimethylamine (500 µl) and the resultant mixture is agitated at ambient temperature for 16 hours. The reaction mixture is concentrated to dryness and the residue is purified by a column chromatography (SiO$_2$, CH$_2$Cl$_2$/MeOH: 100/0 to 90/10) followed by crystallization with acetonitrile, resulting in 102 mg of the sought compound.

15.b. 11-(dimethylamino)methyl-5-ethyl-4,5-dihydro-5,10-dihydroxy-1H-oxepino [3',4':6,7]-indolizino [1,2-b] quinoline-3,15 (4H,13H)-dione chlorhydrate Diluted hydrochloric acid (1N) is added drop-wise to a suspension of 11-dimethylamino)methyl-5-ethyl-4,5-dihydro-5,10-dihydroxy-1H-oxepino [3',4':6,7]-indolizino [1,2-b] quinoline-3,15 (4H,13H)-dione (102 mg) in water, until completely dissolved. The water is evaporated under reduced pressure and the residue is put into suspension in acetonitrile (5 ml) and filtered, resulting in 103 mg of the sought salt, m.p. 248° C. (d).

NMR-$^1$H (DMSO): 0.88 (t, 3H); 1.85 (m, 2H); 2.84 (s, 6H); 3.08 (d, 1H); 3.5 (d, 1H); 4.73 (s, 2H); 5.47 (dd, 2H); 7.33 (s, 1H); 7.38 (s, 1H); 7.72 (d, 1H); 8.19 (d, 1H); 8.99 (s, 1H); 9.92 (se, 1H); 11.45 (s, 1H).

NMR-C$^{13}$ (DMSO): 8.46; 34.36; 42.44 (3C); 50.61 (2C); 61.42; 73.35; 99.19; 108.63; 122.21; 122.36; 126.86; 129.13; 130.61; 133.09; 143.53; 144.70; 149.76; 155.98; 157.17; 159.27; 172.06.

EXAMPLE 16

5-ethyl-9-fluoro-4,5-dihydro-5-hydroxy-10-methoxy-1H-oxepino [3',4':6,7] indolizino [1,2-b] quinoline-3,15 (4H,13H)-dione This compound is obtained from 3-fluoro-4-methoxyaniline according to the method illustrated by the stages 11.i, 11.j, and 11.k of example 11. Yellow solid, m.p. >250° C.

NMR-$^1$H (DMSO): 0.89 (t, 3H); 1.85 (q, 2H); 3.08 (d, 1H); 3.49 (d, 1H); 4.00 (s, 3H); 5.25 (s, 2H); 5.39 (d, 1H); 5.51 (d, 1H); 6.00 (s, 1H); 7.32 (s, 1H); 7.72 (d, 1H); 7.91 (d, 1H); 8.58 (s,1H).

NMR-C$^{13}$ (DMSO): 8.43; 36.48; 42.51; 50.68; 56.60; 61.42; 73.29; 99.25; 108.68; 113.52; 122.23; 126.33; 129.99; 130.30; 143.79; 144.70; 148.42; 151.18; 153.19; 155.81; 159.20; 172.06.

IR (KBr): 1259; 1503; 1602; 1737.

EXAMPLE 17

9-chloro-5-ethyl-4,5-dihydro-5-hydroxy-10-methyl-1H-oxepino [3',4':6,7] indolizino [1,2-b] quinoline-3,15 (4H,13H)-dione This compound is obtained from 3-chloro-4-methoxyaniline according to the method illustrated by the stages 11.i, 11.j, and 11.k of example 11. Yellow solid, m.p. >250° C.

NMR-$^1$H (DMSO): 0.85 (t, 3H); 1.85 (q, 2H); 2.55 (s, 3H); 3.07 (d, 1H); 3.45 (d, 1H); 5.25 (s, 2H); 5.39 (d, 1H); 5.51 (d, 1H); 6.05 (s, 1H); 7.39 (s, 1H); 8.10(s, 1H); 8.20(s,1H); 8.60(s,1H).

NMR-C$^{13}$ (DMSO): 8.43; 20.20; 36.47; 42.49; 50.67; 61,41; 73.28; 99.87; 122.82; 126.98; 127.99; 129.60; 130.53; 131.08; 135.64; 136.56; 144.39; 147.11; 153.10; 155.85; 159.18; 172.03.

IR (KBr): 1208; 1479; 1606; 1656; 1724.

EXAMPLE 18

5-ethyl-9,10-difluoro-4,5-dihydro-5-hydroxy-1H-oxepino [3',4':6,7] indolizino [1,2-b] quinoline-3,15 (4H,13H)-dione This compound is obtained from 3,4-difluoroaniline according to the method illustrated by the stages 11.i, 11.j, and 11.k of example 11. Yellow solid, m.p. >250° C.

NMR-$^1$H (DMSO): 0.85 (t, 3H); 1.85 (q, 2H) ; 3.07 (d, 1H); 3.47 (d, 1H); 5.25 (s, 2H); 5.39 (d, 1H); 5.51 (d, 1H); 6.05 (s, 1H); 7.39 (s, 1H); 8.15(q, 1H); 8.25(q,1H); 8.68(q, 1H).

NMR-C¹³ (DMSO): 8.41; 36.45; 42.48; 50.68; 61.40; 73.25; 99.92; 114.14; 115.42; 115.58; 122.96; 125.52; 130.56; 131.46; 144.21; 145.25; 142.36; 153.41; 155.85; 159.15; 172.00.

IR (KBr): 1266; 1512; 1581; 1618; 1751.

EXAMPLE 19

7-ethyl-7,8-dihydro-7-hydroxy-9H,11H-[1,3]
dioxole [4,5-g] oxepino [3',4':6,7] indolizino [1,2-b]
quinoline-9,12 (14H)-dione This compound is obtained from 3,4-methylenedioxyaniline according to the method illustrated by the stages 11.i, 11.j, and 11.k of example 11. Beige solid, m.p. >250° C.

NMR-¹H (DMSO): 0.85 (t, 3H); 1.85 (q, 2H) ; 3.07 (d, 1H); 3.45 (d, 1H); 5.20 (s, 2H); 5.39 (d, 1H); 5.51 (d, 1H); 6.00 (s, 1H); 6.30 (s, 1H); 7.30(s, 1H); 7.49(d,2H); 8.45(s, 1H).

NMR-C¹³ (DMSO): 8.43; 36.49; 42.56; 50.58; 61.42; 73.31; 98.87; 102.75; 103.33; 104.92; 121.76; 125.74; 128.59; 130.33; 145.08; 146.69; 148.78; 150.19; 151.49; 155.90; 159.24; 172.08.

IR (KBr): 1248; 1459; 1606; 1731.

EXAMPLE 20

9-chloro-5-ethyl-4,5-dihydro-5-hydroxy-10-methoxy-1H-oxepino [3',4':6,7] indolizino [1,2-b]
quinoline-3,15 (4H,13H)-dione This compound is obtained from 3-chloro-4-methoxyaniline according to the method illustrated by the stages 11.i, 11.j, and 11.k of example 11. White solid, m.p. >250° C.

NMR-¹H (DMSO): 0.85 (t, 3H); 1.85 (q, 2H) ; 3.07 (d, 1H); 3.45 (d, 1H); 4.01 (s, 3H); 5.22 (s, 2H); 5.39 (d, 1H); 5.51 (d, 1H); 6.02 (s, 1H); 7.31 (s, 1H); 7.68(s, 1H); 8.20(s, 1H); 8.55(s,1H).

NMR-C¹³ (DMSO): 8.82; 36.27; 42.30; 50.48; 56.69; 61.23; 73.08; 99.16; 107.44; 122.16; 127.12; 128.12; 128.25; 130.02; 130.53; 143.29; 144.37; 151.12; 153.29; 155.71; 158.98; 171.84.

IR (KBr): 1056; 1256; 1483; 1592; 1657; 1747.

EXAMPLE 21

5-ethyl-4,5-dihydro-5-hydroxy-10-methoxy-1H-oxepino [3',4':6,7] indolizino [1,2-b] quinoline-3,15
(4H,13H)-dione This compound is obtained from 4-methoxyaniline according to the method illustrated by the stages 11.i, 11.j, and 11.k of example 11. Yellow solid, m.p. >250° C.

NMR-¹H (DMSO): 0.85 (t, 3H); 1.85 (q, 2H) ; 3.07 (d, 1H); 3.45 (d, 1H); 3.95 (s, 3H); 5.28 (s, 2H); 5.40 (d, 1H); 5.51 (d, 1H); 6.00 (s, 1H); 7.38 (s, 1H); 7.51(d, 2H); 8.07(d,1H); 8.55(s,1H).

NMR-C¹³ (DMSO): 8.45; 36.48; 42.51; 50.64; 55.92; 61.42; 73.33; 99.01; 106.49; 122.02; 123.19; 129.59; 130.20; 130.43; 144.17; 144.94; 150.40; 155.92; 158.31; 159.26; 172.07.

IR (KBr): 1251; 1604; 1655; 1735.

EXAMPLE 22

9,11-dichloro-5-ethyl-4,5-dihydro-5-hydroxy-1H-oxepino [3',4':6,7] indolizino[1,2-b] quinoline-3,15
(4H,13H)-dione This compound is obtain from 3,5-dichloroaniline according to the method illustrated by the stages 11.i, 11.j, and 11.k of example 11. Yellow solid, m.p. >250° C.

NMR-¹H (DMSO): 0.85 (t, 3H); 1.85 (q, 2H) ; 3.07 (d, 1H); 3.45 (d, 1H); 5.30 (s, 2H); 5.41 (d, 1H); 5.55 (d, 1H); 6.08 (s, 1H); 7.41 (s, 1H); 8.05(s, 1H); 8.21(s,1H); 8.91(s, 1H).

NMR-C¹³ (DMSO): 8.93; 36.45; 42.51; 51.03; 61.39; 73.25; 100.62; 123.55; 124.63; 127.60; 128.08; 128.56; 132.06; 132.19; 134.53; 143.77; 148.80; 154.88; 155.82; 159.13; 171.98.

IR (KBr): 1064; 1275; 1586; 1651; 1743.

EXAMPLE 23

5-ethyl-9-fluoro-4,5-dihydro-5-hydroxy-10-methyl-1H-oxepino [3',4':6,7] indolizino [1,2-b] quinoline-
3,15 (4H,13H)-dione This compound is obtained from 3-fluoro-4-methylaniline according to the method illustrated by the stages 11.i, 11.j, and 11.k of example 11. Yellow solid, m.p. >250° C.

NMR-¹H (DMSO):: 0.89 (t, 3H); 1.85 (q, 2H); 2.49 (s, 3H); 3.08 (d, 1H); 3.49 (d, 1H); 5.21 (s, 2H); 5.39 (d, 1H); 5.51 (d, 1H); 6.05 (s, 1H); 7.39 (s, 1H); 7.87(d, 1H); 8.05(d,1H); 8.61(s,1H).

NMR-C¹³ (DMSO): 8.40; 15.14; 36.45; 42.52; 50.60; 61.41; 73.28; 99.71; 112.00; 122.66; 125.38; 127.66; 129.59; 130.28; 144.49; 147.88; 152.88; 155.85; 159.18; 162.25; 172.02.

IR (KBr): 1054; 1580; 1651; 1760.

EXAMPLE 24

5-ethyl-10-fluoro-4,5-dihydro-5-hydroxy-1H-oxepino [3',4':6,7] indolizino [1,2-b] quinoline-3,15
(4H,13H)-dione This compound is obtained from 4-fluoroaniline according to the method illustrated by the stages 11.i, 11.j, and 11.k of example 11. White solid, m.p. >250° C.

NMR-¹H (DMSO): 0.85 (t, 3H); 1.85 (q, 2H); 3.07 (d, 1H); 3.45 (d, 1H); 5.29 (s, 2H); 5.39 (d, 1H); 5.55(d, 1H); 6.30 (s, 1H); 7.39 (s, 1H); 7.80(q, 1H); 7.99(q,1H); 8.23(q, 1H); 8.68 (s,1H).

NMR-C¹³ (DMSO): 8.40; 36.46; 42.48; 50.66; 61.41; 73.31; 99.68; 111.83; 122.75; 128.93; 130.93; 131.22; 131.93; 144.46; 145.27; 152.60; 155.89; 159.21; 172.04.

IR (KBr): 1209; 1589; 1659; 1739.

EXAMPLE 25

10-chloro-5-ethyl-4,5-dihydro-5-hydroxy-1H-oxepino [3',4':6,7] indolizino [1,2-b] quinoline-3,15
(4H,13H)-dione This compound is obtained from 4-chloroaniline according to the method illustrated by the stages 11.i, 11.j, and 11.k of example 11. Yellow solid, m.p. >250° C.

NMR-¹H (DMSO): 0.85 (t, 3H); 1.85 (q, 2H) ; 3.07 (d, 1H); 3.47 (d, 1H); 5.25 (s, 2H); 5.39 (d, 1H); 5.51(d, 1H); 6.05(s, 1H); 7.39 (s, 1H); 7.89(d, 1H); 8.19(d,1H); 8.29(s, 1H); 8.67 (s,1H).

NMR-C¹³ (DMSO): 8.40; 36.46; 42.48; 50.70; 61.42; 73.31; 100.00; 122.96; 127.31; 127.42; 128.87; 131.11; 132.12; 144.34; 146.53; 153.38; 155.88; 159.20; 172.04.

IR (KBr): 1069; 1483; 1606; 1741.

EXAMPLE 26

10-chloro-5-ethyl-9-fluoro-4,5-dihydro-5-hydroxy-
1H-oxepino [3',4':6,7] indolizino [1,2-b] quinoline-
3,15 (4H,13H)-dione This compound is obtained from 4-chloro-3-fluoroaniline according to the method illustrated by the stages 11.i, 11.j, and 11.k of example 11. Yellow solid, m.p. >250° C.

NMR-¹H (DMSO): 0.85 (t, 3H); 1.85 (q, 2H); 3.07 (d, 1H); 3.45 (d, 1H); 5.25 (s, 2H); 5.39 (d, 1H); 5.51(d, 1H); 6.05(s, 1H); 7.40 (s, 1H); 8.20(d, 1H); 8.40(d,1H); 8.68 (s,1H).

NMR-C¹³ (DMSO): 8.38; 36.47; 42.58; 50.71; 61.40; 73.26; 99.99; 133.59; 123.09; 124.28; 127.74; 130.64; 131.31; 144.13; 145.08; 153.57; 154.13; 155.84; 156.61; 159.14; 172.00.

IR (KBr): 1488; 1583; 1655; 1743.

EXAMPLE 27

5,12-diethyl-4,5-dihydro-5,10-dihydroxy-11-morpholino methyl-1H-oxepino [3',4':6,7] indolizino [1,2-b] quinoline-3,15 (4H,13H)-dione This compound is obtained from morpholine according to the method illustrated in the example 15a. White solid, m.p. >250° C.

NMR-¹H (DMSO): 0.85 (t, 3H); 1.87 (q, 2H); 2.53 (s, 4H); 3.03 (d, 1H); 3.45 (d, 1H); 3.57 (s,4H); 4.02 (s, 2H); 5.01 (s, 2H); 5.38 (d, 1H); 5.52(d, 1H); 6.0(se, 1H); 7.30 (s, 1H); 7.42(d, 1H); 7.95 (d,1H); 8.82(s,1H).

NMR-C¹³ (DMSO): 8.45; 3.49; 42.58; 53.04; 61.44; 66.33; 73.33; 98.81; 113.78; 121.81; 122.74; 126.80; 129.05; 129.91; 143.72; 145.07; 149.24; 155.06; 156.92; 159.28; 172.08.

IR (KBr): 1515; 1595; 1654; 1736.

EXAMPLE 28

5,12-diethyl-9-fluoro-4,5-dihydro-5-hydroxy-10-methoxy-1H-oxepino [3',4':6,7] indolizino [1,2-b] quinoline-3,15 (4H,13H)-dione

28.a. 5-fluoro-4-methoxy-2-propionylaniline (This product is obtained according Sugasawa T., Toyoda T., Adachi M., Saskura K., *J. Am. Chem. Soc.*, 100 (1978), pp. 4842–4852). A solution of 3-fluoro-4-methoxyaniline (20 g, 142 mmol) in anhydrous dichloromethane (200 ml), under an argon atmosphere and at 0° C., is added drop-wise to boron trichloride (1 M in heptane, 156 ml, 156 mmol). The pink suspension thus obtained is maintained under agitation 5 min. Then propionitril (33 ml, 420 mmol) followed by aluminum trichloride (20.9 g, 156 mmol) is added drop-wise in small portions. The reaction medium is heated to reflux for 3 h, chilled at 0° C., hydrolyzed by adding, carefully, 2N hydrochloric acid (100 ml), then brought to reflux for 45 min. After chilling to 0° C., a precipitate is obtained which is then filtered, washed with dichloromethane, then recovered in water (300 ml). The aqueous phase is basified to an alkaline pH, extracted with dichloromethane then ethyl acetate. The organic phase is dried (MgSO₄) then evaporated resulting in a crude product which is purified by column chromatography (SiO₂, AcOEt/Hpt: 1/99 to 20/80). 15.3 g of a yellow solid is obtained.

NMR-1H (CDCl3): 1.20 (t, 3H); 2.92 (q, 2H); 3.83 (s, 3H); 6.2 (s, 2H); 6.40 (d, 2H); 7.32 (d, 2H).

IR (KBr): 857; 1148; 1240; 1561; 1583; 1662.

28.b. ethyl 4-ethyl-7-fluoro-2-hydroxy-6-methoxy-3-quinolinecarboxylate

A solution of 5-fluoro-4-methoxy-2-propionylaniline (15.3 g, 77.5 mmol) and triethylamine (13.9 ml, 100 mmol) in anhydrous acetonitrile (110 ml), under argon and at 0° C., is added drop-wise to a solution of ethylmalonyl chloride (12.9 ml, 100 mmol) in anhydrous acetonitrile (30 ml). The reaction medium is left to return to ambient temperature, a solution of sodium ethylate (obtained with 1.8 g, 78 mmol, of sodium in 80 ml of ethanol), then is left to agitate for 12 hours at ambient temperature. The reaction mixture is poured into ice water (100 ml) and agitated for 2 hours, then the precipitate is filtered and washed with water, ethanol and ether. 19.4 g of a white solid is obtained.

NMR-¹H (CDCl₃): 1.25 (m, 6H); 2.78 (q, 2H); 3.92 (s, 3H); 4.30 (q, 2H); 7.15 (d,2H); 7.40 (d, 2H); 11.93 (s, 1H).

IR (KBr): 786; 1083; 1410; 1521; 1644; 1725.

28.c. ethyl 2-chloro-4-ethyl-7-fluoro-6-methoxy-3-quinolinecarboxylate

A suspension of ethyl 4-ethyl-7-fluoro-2-hydroxy-6-methoxy-3-quinolinecarboxylate (19.4 g, 0.066 mol) in phosphoryl chloride (243 ml) is brought to reflux for 6 h. The phosphoryl chloride is distilled. The reaction mixture is poured into ice water. Recover with dichloromethane to make soluble. The organic phase is washed with water, then with a saturated solution of sodium chloride. The organic phase is dried on magnesium sulfate and the solvent is evaporated. The residue is suspended in ether and filter the non-converted starting product (4 g) is filtered. The filtrate is evaporated and the residue is purified by column chromatography (SiO2, AcOEt/Hpt: 5/95 to 20/80). 10.9 g of a white solid is obtained.

NMR-1H (CDCl3): 1.30 (t, 3H); 1.39 (t, 3H); 3.08 (q, 2H); 4.09 (s, 3H); 4.49 (q, 2H); 7.64 (d, 2H); 7.86 (d, 2H).

IR (KBr): 865; 1016; 1082; 1190; 1224; 1253; 1272; 1508; 1571; 1732.

28.d. 2-chloro-4-ethyl-7-fluoro-6-methoxy-3-quinolinemethanol

A solution of ethyl 2-chloro-4-ethyl-7-fluoro-6-methoxy-3-quinolinecarboxylate (10.8 g, 35 mmol) in anhydrous dichloromethane (200 ml) is treated drop-wise at ambient temperature under inert atmosphere with diisobutylaluminum hydride (1M in dichloromethane, 65 ml, 65 mmol), then heated to 40° C. for 4 h. Chilled to 0° C., a 20% aqueous solution of Rochelle salt is added carefully and dichloromethane (200 ml) and the agitation is maintained for 1 h. Decant, wash three times with water, and dry the organic phase on magnesium sulfate and evaporate the solvent. The residue is purified by column chromatography (SiO2, AcOEt/Hpt: 5/95 to 50/50). 6 g of a white solid is obtained.

NMR-¹H (CDCl3): 1.28 (t, 3H); 3.25 (q, 2H); 4.04 (s, 3H); 4.77 (d, 2H); 5.27 (t, 1H); 7.55 (d, 2H); 7.73 (d, 2H).

IR (KBr): 840; 864; 1023; 1232; 1267; 1317; 1444; 1511; 1569.

28.e. 5,12-diethyl-9-fluoro-4,5-dihydro-5-hydroxy-10-methoxy-1H-oxepino [3',4':6,7] indolizino [1,2-b] quinoline-3,15 (4H,13H)-dione 2-chloro-4-ethyl-7-fluoro-6-methoxy-3-quinolinemethanol is coupled to compound (M) as described in stage 11.j. of example 11. The resultant coupling product is cyclized according to the procedure of stage 11.k. A yellow solid is obtained, m.p. >275° C.

NMR-¹H (CF₃COOD): 1.07 (m, 3H); 1.62 (m, 3H); 2.27 (m, 2H); 3.44 (d,1H); 3.54 (m, 2H); 3.91 (d, 1H); 4.25 (s, 3H); 5.60 (d, 1H); 5.74 (s, 2H); 5.98 (d, 1H); 7.85 (m, 1H); 8.16 (m, 1H); 8.31 (s, 1H).

NMR-C¹³ (CF3COOD): 9.03; 14.20; 26.68; 38.77; 43.98; 53.79; 58.27; 64.73; 77.93; 106.85; 109.24; 110.15; 128.99;

129.20; 131.61; 137.32; 141.23; 144.13; 154.79; 158.32; 160.25; 160.81; 179.30.

IR (KBr): 1013; 1068; 1265; 1466; 1514; 1601; 1655; 1748.

EXAMPLE 29

5-ethyl-4,5-dihydro-5-hydroxy-12-methyl-1H-oxepino [3',4':6,7] indolizino [1,2-b] quinoline-3,15 (4H,13H)-dione 2-acetylaniline is applied to the procedures described by the examples 28.b., 28.c. and 28.d. resulting in 2-chloro-4-methyl-3-quinolinemethanol. The latter is coupled to compound (M) as describe in stage 11.j. of example 11. The resultant coupling product is cyclized according to the procedure of stage 11.k. A yellow solid is obtained, m.p. >260° C.

NMR-$^1$H (DMSO): 0.87 (t, 3H); 1.87 (q, 2H); 2.78 (s, 3H); 2.80 (d, 1H); 3.55 (d, 1H); 5.27 (s, 2H); 5.42 (d, 1H); 5.52 (d, 1H); 6.04 (s, 1H); 7.39 (s, 1H); 7.75 (t, 1H); 7.88 (t, 1H); 8.13 (d, 1H); 8.25 (d, 1H). NMR-C$^{13}$ (DMSO): 8.23; 36.26; 42.36; 62.00; 73.11; 78.65; 79.13; 79.25; 99.52; 122.36; 124.30; 127.67; 129.54; 129.55; 129.56; 140.11; 145.06; 148.07; 152.00; 155.79; 159.09; 171.89.

IR (KBr): 1649; 1751; 3404.

EXAMPLE 30

9-chloro-5-ethyl-4,5-dihydro-5-hydroxy-10-methoxy-12-(4-methyl piperazinomethyl)-1H-oxepino [3',4':6,7] indolizino [1,2-b] quinoline-3,15 (4H,13H)-dione

30.a. 5-chloro-2-chloroacetyl-4-methoxyaniline

This product is obtained according to Sugasawa T., Toyoda T., Adachi M., Sasakura K., *J. Am. Chein. Soc.,* 100 (1978), p. 4842–4852). A molar solution of boron trichloride in hexane (164 ml, 164 mmol), chloroacetonitrile (11.4 ml, 180 mmol), and a molar solution of diethylaluminum chloride in hexane (164 ml, 164 mmol) is added drop-wise in succession to a solution of 3-chloro-4-methoxy-aniline (23.6 g, 150 mmol) in an inert atmosphere at 0° C. The reaction medium is heated to reflux for 1 h then cooled to 0° C., hydrolized by adding carefully 2N hydrochloric acid (90 ml), then maintained at reflux for 1 h. It is chilled again and a concentrated solution of sodium bicarbonate is added to pH 14. The solution is extracted with ethyl acetate, the organic phase is washed in water, then in salt water. Dry it on magnesuim sulfate, filter and evaporate under reduced pressure. The residue is recovered in isopentane, decanted, then recover what is insoluble in the minimum amount of isopropyl ether, and isopentane is added to precipitate the product. Filter and dry under vacuum. 17.26 g of a brown solid are obtained.

NMR-$^1$H (CDCl$_3$): 3.82 (s, 3H); 4.60 (s, 2H); 6.11 (s, 2H); 6.78 (s, 1H); 7.11 (s, 1H).

30.b. ethyl 7-chloro-4-chloromethyl-2-hydroxy-6-methoxy-3-quinolinecarboxylate Ethylmalonyl chloride (17 ml, 131 mmol) is added drop-wise to a solution of 5-chloro-2-chloroacetyl-4-methoxyaniline (17 g, 73 mmol) and triethylamine (18.5 ml, 131 mmol) in anhydrous acetonitrile (310 ml), under argon and at 0° C. Agitate for 2 h at ambient temperature, then add drop-wise at 0° C. a solution of sodium ethanolate in ethanol (obtained by 1.88 g, 80 mmol, of sodium in 90 ml of ethanol). Agitated for 12 hours at ambient temperature. Add 300 ml of water, agitate for another 20 minutes. Filter the precipitate; wash with water, ethanol, and ethyl ether. After drying in vacuum, 16.7 g of a yellowish solid is obtained.

NMR-$^1$H (DMSO): 1.31(t, 3H); 3.95 (s, 3H); 4.36 (q, 2H); 4.95 (s, 2H); 7.46 (s, 1H); 7.49 (s, 1H).

30.c. ethyl 2,7-chloro-4-chloromethyl-6-methoxy-3-quinoline-carboxylate

A suspension of ethyl 7-chloro-4-chloromethyl-2-hydroxy-6-methoxy-3-quinolinecarboxylate (116.7 g, 50 mmol) in phosphoryl chloride (100 ml) is brought to reflux for 6 hours. The phosphoryl chloride is distilled. The residue is recovered in water and agitated for 30 min. The precipitate is filtered and washed with water until neutralization. The precipitate is recovered in dichloromethane and with a saturated solution of sodium chloride. Filter on a bed of celite and decant the filtrate. The organic phase is washed again by a saturated solution of sodium chloride. Dry on magnesium sulfate, and filter and evaporate under reduced pressure. 15.88 g of a brown oil is obtained.

NMR-$^1$H (CDCl$_3$): 1.47 (t, 3H); 4.08 (t, 3H); 4.55 (q, 2H); 4.87 (s, 2H); 7.35 (s, 1H); 8.09 (s, 1H).

30.d. ethyl 2,7-chloro-6-methoxy-4-(4-methylpiperazinomethyl)-3-quinolinecarboxylate A mixture of ethyl 2,7-chloro-4-chloromethyl-6-methoxy-3-quinoline-carboxylate (6.9 g, 20 mmol) and N-methylpiperazine (9 ml, 80 mmol) is heated to 60° C. for 30 min. The reaction mass is diluted in water and extracted with ethyl acetate. Decant and wash the organic phase with water. Dry on magnesium sulfate, filter and evaporate under reduced pressure. Recover the residue in water, agitate 15 minutes, filter, wash with water and dry in a vacuum. Purify the residue by column chromatography (SiO$_2$, MeOH/CH$_2$Cl$_2$: 5/95 to 8/92). 6.7 g of a beige solid product is obtained.

NMR-$^1$H (CDCl$_3$): 1.45 (t, 3H); 2.28 (s, 3H); 2.35–2.70 (m, 8H); 3.86 (s, 2H); 4.04 (s, 3H); 4.48 (q, 2H); 7.77 (s, 1H); 8.05 (s, 1H).

30.e. 2,7-chloro-6methoxy-4-(4-methylpiperazinomethyl)-3-quinolinemethanol

Ethyl 2,7-chloro-6-methoxy-4-(4-methylpiperazinomethyl)-3-quinoline-carboxylate (6 g, 14.5 mmol) is dissolved in methylene chloride (120 ml). A molar solution of diisobutyl aluminum hydride in methylene chloride (60 ml, 60 mmol) is added slowly. Agitate one hour at ambient temperature. Pour the reaction mass slowly into 300 ml of a 20% Rochelle salt solution. Agitate one hour; filter on celite; decant, wash the organic phase with a saturated solution of sodium chloride. Dry on magnesium sulfate, filter and evaporate under reduce pressure. Recover the solid with isopropyl ether, filter and dry in vacuum. 4.3 g of the sought compound is obtained in the form of a yellow solid.

NMR-$^1$H (CDCl$_3$): 2.27 (s, 3H); 2.30 - 2.80(m, 8H); 4.03 (s, 3H); 4.08 (s, 2H); 4.96 (s, 2H); 5.95 (s, 1H); 7.37 (s, 1H); 8.05 (s, 1H).

30.f. 9-chloro-5-ethyl-4,5-dihydro-5-hydroxy-10-methoxy-12-(4-methyl piperazinomethyl)-1H-oxepino [3',4':6,7] indolizino [1,2-b] quinoline-3,15 (4H,13H)-dione 2,7-chloro-6methoxy-4-(4-methylpiperazinomethyl)-3-quinoline-methanol is coupled to compound (M) as described in stages 11.j. of example 11. The resultant coupling product is cyclized according to the procedure outlined in 11.k. A yellow solid is obtained, m.p. >250° C.

NMR-$^1$H (DMSO): 0.87 (t, 3H); 1.84 (q, 2H); 2.53 (s, 4H); 3.08 (d, 1H); 3.47 (d, 1H); 3.58 (s, 4H); 4.06 (s, 5H); 5.30 (s, 2H); 5.42 (q, 2H); 6.03 (s, 1H); 7.31 (s, 1H); 7.91 (s, 1H); 8.16 (s, 1H).

NMR-C$^{13}$ (DMSO): 8.42; 36.53; 50.65; 53.30; 56.67; 62.00; 66.50; 73.32; 99.31; 104.86; 122.32; 126.94; 126.70; 129.83; 130.44; 138.89; 144.22; 144.85; 151.05; 153.17; 155.92; 159.19; 172.06.

IR (KBr): 862; 1063; 1116; 1248; 1595; 1655; 1744; 3449.

EXAMPLE 31

9-chloro-5-ethyl-4,5-dihydro-5-hydroxy- 10-methoxy-12morpholinomethyl-1H-oxepino [3',4':6, 7] indolizino [1,2-b] quinoline-3,15 (4H,13H)-dione Apply 3-chloro-4-methoxyaniline to the procedure described in the examples 30.a., 30.b. and 30.c. resulting in ethyl 2,7-dichloro-4-chloromethyl-6-methoxy-3-quinolinecarboxylate which is treated according to the procedure in example 30.d., using morpholine in place of N-methylpiperazine, then reduce the solution according to the method in example 30.e. in corresponding quinolinemethanol. The latter is coupled to compound (M) as described in step 11.j. of example 11. The resultant coupling product is cyclized according to the procedure outlined in 11.k. A beige solid is obtained, m.p. >250° C.

NMR-$^1$H (DMSO): 0.87 (t, 3H); 1.84 (q, 2H); 2.15 (s, 3H); 2.32 (s, 4H); 2.50 (s, 4H); 3.08 (d, 1H); 3.47 (d, 1H); 4.06 (s, 5H); 5.29 (s, 2H); 5.46 (q, 2H); 6.06 (s, 1H); 7.31 (s, 1H); 7.92 (s, 1H); 8.17 (s, 1H).

NMR-C$^{13}$ (DMSO): 8.42; 36.51; 42.57; 45.93; 50.66; 52.83; 55.05; 56.09; 56.72; 61.44; 73.29; 99.30; 104.89; 122.32; 126.89; 127.63; 129.85; 130.16; 138.78; 144.18; 144.81; 151.03; 153.01; 155.10; 159.17; 172.07.

IR (KBr): 1055; 1252; 1596; 1655; 1747; 3449.

EXAMPLE 32

5-ethyl-4,5-dihydro-5-hydroxy-12-(4-methyl piperazinomethyl)-1H-oxepino [3',4':6,7] indolizino [1,2-b] quinoline-3,15 (4H,13H)-dione Apply aniline to the procedures described in the examples 30.a., 30.b. and 30.c. resulting in ethyl 2-chloro-4-chloromethyl-3-quinolinecarboxylate which is treated according to the procedure in example 30.d. with N-methylpiperazine, then reduced according to the method in example 30.e. in corresponding quinolinemethanol. The latter is coupled to compound (M) as described in step 11.j. of example 11. The resultant coupling product is cyclized according to the procedure outlined in 11.k. A yellow solid is obtained, m.p. >260° C.

NMR-$^1$H (DMSO): 0.86 (t, 3H); 1.87 (q, 2H); 2.14 (s, 3H); 2.32–2.60 (m, 8H); 3.05 (d, 1H); 3.48 (d, 1H); 4.09 (q, 2H); 5.42 (d, 1H), 5.52 (d, 1H); 6.03 (se, 1H); 7.40 (s, 1H); 7.72 (t, 1H); 7.85 (t, 1H); 8.16 (d, 1H); 8.45 (d, 1H).

IR (KBr): 1652; 1735; 3424.

EXAMPLE 33

5-ethyl-4,5-dihydro-5-hydroxy-12-piperidinomethyl-1H-oxepino [3',4':6,7] indolizino [1,2-b] quinoline-3,15 (4H,13H)-dione Apply aniline to the procedures described in the examples 30.a., 30.b. and 30.c. resulting in ethyl 2-chloro-4-chloromethyl-3-quinolinecarboxylate which is treated according to the procedure in example 30.d. by using piperidine in place of N-methylpiperazine, then reduced according to the method in example 30.e. in corresponding quinolinemethanol. The latter is coupled to compound (M) as described in step 11.j. of example 11. The resultant coupling product is cyclized according to the procedure outlined in 11.k. A yellow solid is obtained, m.p. >260° C.

NMR-$^1$H (DMSO): 0.86 (t, 3H); 1.40 (se, 2H); 1.48 (se, 4H); 1.87 (q, 2H); 2.50 (s,4H); 3.05 (d, 1H); 3.48 (d, 1H); 4.04 (q, 2H); 5.33 (s, 2H); 5.42 (d, 1H); 5.51 (d, 1H); 6.07 (se, 1H); 7.75 (t, 1H); 7.85 (t,1H); 8.15 (d, 1H); 8.45 (d, 1H).

NMR-C$^{13}$ (DMSO): 8.47; 23.50; 25.82; 36.50; 42.50; 50.68; 54.47; 58.00; 61.42; 73.35; 99.55; 122.61; 125.31; 127.58; 129.54; 129.55; 129.56; 129.57; 140.49; 144.95; 148.63; 152.41; 155.90; 159.23; 172.07.

IR (KBr): 1659; 1727; 3408.

EXAMPLE 34

5-ethyl-4,5-dihydro-5-hydroxy-12-morpholinomethyl-1H-oxepino [3',4':6,7] indolizino [1,2-b] quinoline-3,15 (4H,13H)-dione Apply aniline to the procedures described in the examples 30.a., 30.b. and 30.c. resulting in ethyl 2-chloro-4-chloromethyl-3-quinolinecarboxylate which is treated according to the procedure in example 30.d. by using morpholine in place of N-methylpiperazine, then reduced according to the method in example 30.e. in corresponding quinolinemethanol. The latter is coupled to compound (M) as described in step 11.j. of example 11. The resultant coupling product is cyclized according to the procedure outlined in 11.k. A yellow solid is obtained, m.p. >260° C.

NMR-$^1$H (DMSO): 0.86 (t,3H); 1.87 (q, 2H); 3.05 (d, 1H); 3.30 (s, 4H); 3.49 (d, 1H); 3.55 (se, 4H); 4.10 (q, 2H); 5.35 (s, 2H); 5.40 (d, 1H); 5.54 (d.1H); 6.04 (s, 1H); 7.72 (t, 1H); 7.85 (t, 1H); 8.16 (d, 1H); 8.47 (d, 1H).

NMR-C$^{13}$ (DMSO): 8.42; 36.51; 42.57; 50.68; 53.51; 56.06; 61.42; 66.41; 73.34; 99.56; 122.64; 125.25; 127.56; 129.81; 139.55; 144.92; 148.62; 152.39; 155.89; 159.21; 172.05.

IR (KBr): 1657; 1729; 3347.

EXAMPLE 35

5-etbyl-10-fluoro-4,5-dihydro-5-hydroxy-12-(4methylpiperazinomethyl)-1H-oxepino [3',4':6,7] indolizino [1,2-b] quinoline-3,15 (4H,13H)-dione Apply 4-fluoroaniline to the procedures described in the examples 30.a., 30.b. and 30.c. resulting in ethyl 2-chloro-4-chloromethyl-6-fluoro-3-quinolinecarboxylate which is treated according to the procedure in example 30.d. with N-methylpiperazine, then reduced according to the method in example 30.e. in corresponding quinolinemethanol. The latter is coupled to compound (M) as described in step 11.j. of example 11. The resultant coupling product is cyclized according to the procedure outlined in 11.k. A yellow solid is obtained, m.p. >275° C.

NMR-$^1$H (DMSO): 0.87 (t, 3H); 1.85 (q, 2H); 2.15 (s, 3H); 2.31 (m, 4H); 2.50 (m, 4H); 3.07 (d, 1H); 3.48 (d, 1H); 4.04 (m, 2H); 5.31 (s, 2H); 5.40 (d, 1H); 5.53 (d, 1H); 6.05 (s, 1H); 7.38 (s, 1H); 7.77 (m, 1H); 8.19 (m, 2H).

NMR-C$^{13}$ (DMSO): 8.43; 36.51; 42.54; 45.89; 50.67; 52.92; 54.93; 55.92; 73.32; 99.56; 122.69; 130.43; 132.40; 139.69; 144.70; 145.84; 152.19; 155.90; 159.17; 172.05.

IR (KBr): 836; 1051; 1217; 1291; 1612; 1662; 1726.

EXAMPLE 36

5-ethyl-10-fluoro-4,5-dihydro-5-hydroxy-12morpholinomethyl-1H-oxepino [3',4':6,7] indolizino [1,2-b] quinoline-3,15 (4H,13H)-dione Apply 4-fluoroaniline to the procedures described in the examples 30.a., 30.b. and 30.c. resulting in ethyl 2-chloro-4-chloromethyl-6-fluoro-3-quinolinecarboxylate which is treated according to the procedure in example 30.d. by using morpholine in place of N-methylpiperazine, then reduce according to the method in example 30.e. in corresponding quinolinemethanol. The latter is coupled to compound (M) as described in step 11.j. of example 11. The resultant coupling product is cyclized according to the procedure outlined in 11.k. A beige solid is obtained, m.p. >250° C.

NMR-$^1$H (DMSO): 0.87 (m, 3H); 1.85 (m, 2H); 2.51 (m,4H); 3.06 (d, 1H); 3.48 (d, 1H); 3.56 (m, 4H); 4.05 (m, 2H); 5.34 (s, 2H); 5.40 (d, 1H); 5.53 (d, 1H); 6.04 (s, 1H); 7.38 (s, 1H); 7.77 (m, 1H); 8.21 (m, 2H).

NMR-C$^{13}$ (DMSO): 8.40; 36.47; 42.52; 50.59; 53.40; 56.14; 61.44; 66.41; 73.29; 99.58; 109.05; 109.28; 120.11; 120.37; 122.68; 128.53; 130.53; 132.43; 139.13; 144.62; 145.79; 152.07; 155.94; 159.14; 161.59; 172.04.

IR (KBr): 834; 860; 1061; 1118; 1215; 1286; 1516; 1609; 1658; 1734.

EXAMPLE 37

5-ethyl-9-fluoro-4,5-dihydro-5-hydroxy-10-methyl12-(4-methylpiperazinomethyl)-1H-oxepino [3',4':6,7] indolizino [1,2-b] quinoline-3,15 (4H, 13H)-dione Apply 3-fluoro-4-methylaniline to the procedures described in the examples 30.a., 30.b. and 30.c. resulting in ethyl 2-chloro-4-chloromethyl-7-fluoro-6-methyl-3quinolinecarboxylate which is treated according to the procedure in example 30.d. with N-methylpiperazine, then reduced according to the method in example 30.e. in corresponding quinolinemethanol. The latter is coupled to compound (M) as described in step 11.j. of example 11. The resultant coupling product is cyclized according to the procedure outlined in 11.k. A yellow solid is obtained, m.p. >260° C.

NMR-$^1$H (CDCl$_3$): 1.00 (t, 3H); 2.00 (q, 2H); 2.35 (s, 3H); 2.50 (s, 3H); 2.61 (m, 8H); 3.33 (d, 1H); 3.39 (d, 1H); 3.97 (d, 1H); 4.07 (d, 1H); 5.17 (d, 1H); 5.38 (d, 1H); 5.52 (d, 1H); 5.63 (d, 1H); 7.13 (d, 1H); 7.28 (s, 1H); 7.99 (d, 1H).

IR (KBr): 1652; 1747; 3430.

EXAMPLE 38

5-ethyl-9-fluoro-4,5-dihydro-5-hydroxy-10-methyl-12morpholinomethyl-1H-oxepino [3',4':6,7] indolizino [1,2-b] quinoline-3,15 (4H,13H)-dione Apply 3-fluoro-4-methylaniline to the procedures described in the examples 30.a., 30.b. and 30.c. resulting in ethyl 2-chloro-4-chloromethyl-7-fluoro-6-methyl-3quinolinecarboxylate which is treated according to the procedure in example 30.d. by using morpholine in place of N-methylpiperazine, then reduce according to the method in example 30.e. in corresponding quinolinemethanol. The latter is coupled to compound (M) as described in step 11.j. of example 11. The resultant coupling product is cyclized according to the procedure outlined in 11.k. A yellow solid is obtained, m.p. >260° C.

NMR-$^1$H (DMSO+CDCl$_3$): 1.00 (t, 3H); 2.02 (q, 2H); 2.57 (s, 3H); 2.60 (s, 4H); 3.23 (d, 1H); 3.45 (d, 1H); 3.75 (s, 4H); 4.11 (s, 2H); 5.44 (s, 2H); 5.47 (d, 1H); 5.65 (d, 1H); 7.62 (s, 1H); 7.73 (d, 1H); 8.24 (d, 1H).

NMR-C$^{13}$ (CF$_3$CO$_2$D): 8.35; 13.93; 16.01; 22.24; 25.29; 38.18; 43.42; 54.19; 56.04; 56.74; 64.16; 65.09; 77.48; 108.29; 108.57; 128.07; 128.70; 129.90; 135.64; 138.03; 139.86; 141.10; 141.56; 147.78; 158.30; 161.87; 178.72.

IR (KBr): 117; 1609; 1654; 1750; 3437.

EXAMPLE 39

5-ethyl-9-fluoro-4,5-dihydro-5-hydroxy-10-methyl-12piperidinomethyl-1H-oxepino [3',4':6,7] indolizino [1,2-b] quinoline-3,15 (4H,13H)-dione Apply 3-fluoro-4-methylaniline to the procedures described in the examples 30.a., 30.b. and 30.c. resulting in ethyl 2-chloro-4-chloromethyl-7-fluoro-6-methyl-3-quinolinecarboxylate which is treated according to the procedure in example 30.d. by using piperidine in place of N-methylpiperazine, then reduce according to the method in example 30.e. in corresponding quinolinemethanol. The latter is coupled to compound (M) as described in step 11.j. of example 11. The resultant coupling product is cyclized according to the procedure outlined in 11.k. A yellow solid is obtained, m.p. >260° C.

NMR-$^1$H (CF$_3$CO$_2$D): 1.09 (s, 3H); 1.70 (t, 1H); 2.03 (m, 5H); 2.25 (s, 2H); 2.70 (s,3H); 3.54 (d, 3H); 3.88 (d, 1H); 4.01 (se,2H); 5.30 (q, 2H); 5.65 (d, 1H); 5.96 (d, 1H); 6.10 (s, 2H); 8.16 (d, 1H); 8.35 (s, 1H); 8.61 (s, 1H).

NMR-C$^{13}$ (CF$_3$CO$_2$D): 8.47; 16.07; 20.93; 22.18; 24.76; 38.28; 43.53; 54.30; 56.12; 58.33; 64.24; 77.56; 108.37; 111.30; 128.20; 129.02; 129.98; 135.60; 138.29; 139.90; 141.60; 142.26; 147.57; 158.28; 161.90; 167.63; 170.31; 178.82.

IR (KBr) :1605; 1657; 1728; 3399.

EXAMPLE 40

8-ethyl-2,3,8,9-tetrahydro-8-hydroxy-16-(4-methyl piperazinomethyl)-10H,12H-(1,4) dioxino (2,3-g) oxepino [3',4':6,7] indolizino [1,2-b] quinoline-10, 13[15H]-dione Apply 3,4-ethylenedioxyaniline to the procedures described in the examples 30.a., 30.b. and 30.c. resulting in ethyl 2-chloro-4-chloromethyl-6,7-ethylenedioxy-3quinolinecarboxylate which is treated according to the procedure in example 30.d. with N-methylpiperazine, then reduced according to the method in example 30.e. in corresponding quinolinemethanol. The latter is coupled to compound (M) as described in step 11.j. of example 11. The resultant coupling product is cyclized according to the procedure outlined in 11.k. A yellow solid is obtained, m.p. >260° C.

NMR-$^1$H (DMSO): 0.92 (t, 3H); 1.89 (q, 2H); 2.16 (s, 3H); 2.50 (m, 8H); 3.12 (d, 1H); 3.50 (d, 1H); 3.95 (s, 2H); 4.47 (s, 4H); 5.19 (q, 2H); 5.43 (d, 1H); 5.56 (d, 1H); 7.35 (s, 1H); 7.54 (s, 1H); 7.76 (s, 1H).

NMR-C$^{13}$ (DMSO): 8.45; 24.80; 36.51; 42.48; 45.90; 50.45; 52.98; 54.91; 56.10; 61.44; 64.43; 73.30; 99.03; 109.46; 1 13.5 1; 121.95; 123.51; 127.76; 137.99; 145.00; 145.14; 145.27; 147.24; 150.53; 155.90; 159.18; 172.27; 177.00.

EXAMPLE 41

9-chloro-5-ethyl-10-fluoro-4,5-dihydro-5-hydroxy-12morpholinomethyl-1H-oxepino [3',4':6,7] indolizino [1,2-b] quinoline-3,15 (4H,13H)-dione Apply 3-chloro-4-fluoroaniline to the procedures described in the examples 30.a., 30.b. and 30.c. resulting in ethyl 2,7-dichloro-4-chloromethyl-6-fluoro-6-3-quinolinecarboxylate which is treated according to the procedure in example 30.d. using morpholine in place of N-methylpiperazine, then reduced according to the method in example 30.e. in corresponding quinolinemethanol. The latter is coupled to compound (M) as described in step 11.j. of example 11. The resultant coupling product is cyclized according to the procedure outlined in 11.k. A beige solid is obtained, m.p. >250° C.

NMR-$^1$H (CF$_3$COOD): 1.09 (t, 3H); 2.30 (m, 2H); 3.50 (d, 1H); 3.90 (d, 1H); 3.98 (d, 4H); 4.36 (s, 4H); 5.38 (q, 2H),; 5.64 (d, 1H); 5.96 (d, 1H); 6.23 (q, 2H); 8.57 (d, 1H); 8.60 (s, 1H); 8.85 (d, 1H).

NMR-C$^{13}$ (CF$_3$COOD): 8.10; 37.80; 43.11; 54.31; 55.78; 63.75; 65.11; 77.06; 128.28; 129.55; 130.33; 136.26; 137.11; 138.40; 139.67; 139.85; 148.58; 157.54; 159.74; 161.31; 178.00.

IR (KBr) :848; 1042; 1230; 1609; 1658; 1750; 3310; 3387.

EXAMPLE 42 resolution of 5-ethyl-4,5-dihydro-5-hydroxy-1H-oxepino [3',4':6,7]-indolizino [1,2-b] quinoline-3,15 (4H,13H)-dione A mixture of β-ethyl-β-hydroxy-γ-(8-hydroxymethylindolizino [1,2-b] quinoline-9(11H)-one-7-yl)-propionic acid (19.5 g, 52 mmol) and L-(-)-α-methylbenzylamine (12.12 g, 100 mmol) in absolute ethanol (11) is carried to boiling, hot-filtered and allowed to rest for 68 h. The precipitate is filtered and washed with ethanol and ether resulting in 9.8 g of a white solid. An analysis by high pressure affinity chromatography on the chiral phase ("HPLC chiral" on a Chiral-AGP column (Chromthech, Stockholm, Sweden) 100×4 mm, 2% acetonitrile eluant in a 10 mM, pH 6.9 phosphate buffer, eluant peaks at 4.5 and 7.5 min) reveals two peaks integrating respectively for 24% and 76% of the total surface of the two peaks. Recover the solid in 93% ethanol (350 ml) at reflux, then allow to rest for 48 h. Filter the precipitate then wash with ethanol and ether to obtain 4.8 g of a white solid, giving two integrating peaks respectively for 9% and 91% of the total surface of the two peaks by chiral HPLC. Recover the solid in 50% ethanol (48 ml) at reflux then allow to rest for 48 h. Filter the precipitate then wash with ethanol and ether resulting in 2.7 g of a white solid giving two integrating peaks respectively for 1% and 99% of the total surface of the two peaks by chiral HPLC. The resultant salt is treated, enriched diastereoisomerically, recovered in distilled water (20 ml), with acetic acid (0.35 ml, 6.4 mmol) for 15 min. Filter the precipitate obtained, wash with water, acetone and ether then dry in a vacuum at 80° C. resulting in 1.1 g of a white solid. Recover the latter in absolute ethanol (55 ml) with concentrated hydrochloric acid added (11.5 N, 11 ml) resulting in a yellow solution which is agitated at ambient temperature for 68 h. Filter the precipitate thus obtained and wash with water, ethanol and ether, then dry in vacuum at 80° C. resulting in 770 mg of 5-ethyl-4,5-dihydro-5-hydroxy-1H-oxepino [3',4':6,7]-indolizino [1,2-b] quinoline-3,15 (4H,13H)-dione enantiomerically enriched. An analysis by chiral HPLC (Chiral-AGP column, eluted by a 2 to 5% gradient of acetonitrile in a 10 mM at pH 6.9 phosphate buffer, eluant peaks at 15 and 20 min) reveal an enantiomeric excess of 98%. Repeat the procedure described above replacing the L-(-)-α-methylbenzylamine with D-(+)-α-methylbenzylamine. The other enantiomer of 5-ethyl-4,5-dihydro-5-hydroxy-1H-oxepino [3',4':6,7]-indolizino [1,2-b]quinoline-3,15 (4H, 13H)-dione is thus obtained.

By using the procedures indicated above, the following products may be prepared as well, and are as well part of the invention which constitutes the preferred products:

10-benzyloxy-5,12-diethyl-4,5-dihydro-5-hydroxy-1H-oxepino [3',4':6,7] indolizino [1,2-b] quinoline-3,15 (4H, 13H)-dione;

5,12-diethyl-4,5-dihydro-5,10,-dihydroxy-1H-oxepino [3', 4':6,7] indolizino [1,2-b]quinoline-3,15 (4H,13H)-dione;

5,12-diethyl-4,5-dihydro-5,10-dihydroxy-11-dimethylaminomethyl-1H-oxepino [3',4':6,7] indolizino [1,2-b] quinoline-3,15 (4H,13H)-dione;

5-ethyl-4,5-dihydro-5-hydroxy-9,10-dimethoxy-1H-oxepino [3',4 :6,7] indolizino [1,2-b] quinoline-3,15 (4H,13H)-dione;

10-bromo-5-ethyl-4,5-dihydro-5-hydroxy-1H-oxepino [3', 4':6,7] indolizino [1,2-b] quinoline-3,15 (4H,13H)-dione;

11-bromo-5-ethyl-4,5-dihydro-5-hydroxy-10-methoxy-1H-oxepino [3',4':6,7] indolizino [1,2-b] quinoline-3,15 (4H, 13H)-dione;

5-ethyl-12-dimethylaminomethy-4,5-dihydro-5-hydroxy-1H-oxepino [3',4':6,7] indolizino [1,2-b] quinoline-3,15 (4H,13H)-dione;

5-ethyl-4,5-dihydro-5-hydroxy-1H, 3H-cyclopenta [g] oxepino [3',4':6,7] indolizino [1,2-b] quinoline-3,16 (14H)-dione;

7-ethyl-7,8-dihydro-7-hydroxy-16-(4-methylpiperazino methyl)-9H, 11H-[1,3] dioxolo [4,5-g] oxepino [3',4':6,7] indolizino [1,2-b] quinoline-9,12 (14H)-dione;

5-ethyl-4,5-dihydro-5-hydroxy-12-(1-imidazylmethyl)-1H-oxepino [3',4':6,7] indolizino [1,2-b ] quinoline-3,15 (4H, 13H)-dione;

8-ethyl-8,9-dihydro-8-hydroxy-10H, 12H-oxepino [3',4':6, 7] indolizino [1,2-b] pyrido [2,3-g] quinoline-10,13 (15H)-dione;

5-ethyl-4,5,9,10,11,12-hexahydro-5-hydroxy-1H, 3H-benzo [g] oxepino [3',4':6,7] indolizino [1,2-b] quinoline-3,17 (15H)-dione;

8-ethyl-8,9-dihydro-8-hydroxy-14H, 10H, 12H-[1,3] dioxino [4,5-g] oxepino [3',4':6,7] indolizino [1,2-b] quinoline-10,13 [15H]-dione;

7-ethyl-7,8-dihydro-7-hydroxy-1H, 9H, 11H-oxepino [3', 4':6,7] indolizino [1,2-b] pyrrolo [2,3-g] quinoline-9,12 (14H)-dione;

7-ethyl-7,8-dihydro-7-hydroxy-1H, 9H, 11H-imidazo [4,5-g] oxepino [3',4':6,7] indolizino [1,2-b] quinoline-9,12 (14H)-dione;

7-ethyl-7,8-dihydro-7-hydroxy-1H, 9H, 11H-oxepino [3', 4':6,7] indolizino [1,2-] 1,2,3-triazolo [4,5-g] quinoline-9,12 (14H)-dione;

7-ethyl-7,8-dihydro-7-hydroxy-9H, 11H-oxepino [3',4':6,7] indolizino [1,2-b] thiazolo [4,5-g] quinoline-9,12 (14H)-dione; and 7-ethyl-7,8-dihydro-7-hydroxy-9H, 11H-oxazolo [4,5-g] oxepino [3',4':6,7] indolizino [1,2-b] quinoline-9,12 (14H)-dione.

Pharmacological Study of the Products of the Invention

1. Test of the Activity of the Relaxation Activity of DNA Induced by Topoisomerase 1

All reactions are carried out in a reaction buffer of 20 μl comprised of 50 mM of tris-HCl (pH 7.5), 50 mM of KCl, 0.5 mM of dithiothritol, 10 mM of $MgCl_2$, 0.1 mM of ethyldiamine tetraacetic acid (EDTA), 30 μl/ml bovine albumin serum and 300 ng of coiled pUC19 (Pharmacia Biotech, Orsay, France) with or without compounds to test a defined concentrations. All of the compounds to be tested are dissolved initially in 50 mM of dimethylsulfoxide (DMSO), the other dilutions being made with distilled water. The final concentration in DMSO does not exceed 1% (v/v). The reaction is initiated by the addition of one unit of purified thymus DNA of sheep topoisomerase 1 (Gibco-BRL, Paisley, United Kingdom) and is carried out for 15 minutes at 37° C. The reactions are stopped by the addition of 3 μl of a mixture comprising 1% dodecyl sodium sulfate, 20 mM EDTA and 500 μg/ml of proteinase K (Boehringer Mannheim, Melan, France). After a supplementary incubation period of 30 minutes at 37° C., 2 μl of a charging buffer comprising $Na_2HPO_4$, 0.3% bromophenol blue and 16% Ficoll are added to samples which are subjected to 1.2% to 1 V/cm agar gel electrophoresis for 20 hours in a buffer comprising 36 mM pH 7.8 Tris-HCl, 30 mM $Na_2PO_4$, 1 mM EDTA and 2 μg/ml chloroquin. The gels are dyed with 2 μg/ml ethidium bromide, photographed in 312 nm U.V. light with a photographic appliance and the fluorescent intensity is measured with a bioProfil camera (Vilber Lourmat, Lyon, France) in order to determine the percentage of relaxed DNA. Each experiment is performed at least three times in duplicate.

In each experiment, coiled DNA plasmid is incubated alone or with topoisomerase 1. The reaction is completed in the space of 15 minutes, for each compound tested or used as a control the coiled DNA plasmid is incubated in the presence of 500 μM of the compound to be tested with or without enzyme plus the compound, at concentrations of 10 μM, 100 μM, 200 μM and 500 μM. As indicated in Table 1, examples 2, 3, 4, 9, 10 and 11 inhibit the relaxation activity favored by topoisomerase 1 in a manner dependent upon the dose.

TABLE 1

| | Percentage of Relaxed DNA | | | |
|---|---|---|---|---|
| | Concentration μM | | | |
| Example | 10 | 100 | 200 | 500 |
| Example 2 | 97.9 | 78.3 | 73.2 | 51.1 |
| Example 3 | 79.9 | 59.9 | 55.0 | 45.7 |
| Example 4 | 99.1 | 82.2 | 67.6 | 32.9 |
| Example 9 | 77.1 | 33.9 | 29.7 | 20.4 |
| Example 10 | 96.9 | 45.4 | 26.2 | 8.7 |
| Example 11 | 65.0 | 50.3 | 39.8 | 31.0 |

2. Test of Cell Proliferation

Eight tumor cell lines are used in this study L1210 (mouse lymphocytic leukemia), HCT15 and LOVO (adenocarcinoma cell lines of human colon), A549 (carcinoma of human lung), A172, U373, U87 (human glioblastomas). All of these lines are obtained form the American Type Collection Cultures (ATCC), Rockville, Md. The cultures of the L1210 cells in suspension are cultivated in an eagle medium of modified Dulbecco (DMEM) (BioWhitaker, Verviers, Belgium) completed with 10% fetal calf serum inactivated by heating, 2 mM of glutamine, 50 U/ml of penicillin and 50 μl/ml of streptomycin. The HT29 cells are cultivated in mono-layer cultures in a 5aMcCoy medium (Gibco, Paisley, United Kingdom) completed with 10% fetal calf serum inactivated by heating then adding 2 mM of glutamine and 50 μg of gentamycin. The other cells are cultivated in an essential medium of modified Earle (EMEM; Gibco, Paisley, United Kingdom) completed with 5% fetal calf serum inactivated by heat, 2 mM of glutamine, 50 U/ml of penicillin and 50 μg/ml of streptomycin. All of the cell lines are cultivated at 37° C. in a humidified atmosphere containing 95% air and 5% $CO_2$.

The inhibition of the tumor cell lines is determined by means of an MTT test, 1500 L1210 cells in a medium of culture (according to the needs of the cell medium) are seeded in a well of a microcuvette plaque (level of tissue culture: 96 wells, flat bottom) 24 hours before the treatment with the compounds to be tested. For these dose-response studies, the cells are incubated with each of the compounds to be tested or their corresponding solvent (control) for 48 hours in a final concentration pool of $1.10^{-10}$ to $1.10^{-4}$ M. All the compounds are dissolved just before use in dimethylsulfoxide (DMSO) at a concentration of 50 mM. Other dilutions of medications are carried out in the culture medium. The final concentration of DMSO never exceeds 0.2% (v/v). As control the medication solutions are replaced by the solvent which is successively diluted in the same fashion as the compounds to be tested.

After the incubation period, the marking reagent MTT (3-[4,5-dimethylthiazol-2-yl]-2,5-diphenyltetrazolium; Thiazol bule, Sigma M 565, Sigma, St. Louis Mo.) is added at a final concentration of 0.3 mg/ml to each well. The cells are incubated for 4 hours at 37° C. in a humidified atmosphere. This stage permits the mitochondrial dishydrogenase of the live cells to convert into the yellow tetrazolium salt MTT in purple formazan crystals. The supernatant is eliminated and the formed formazan crystals are solubilized with DMSO. The resultant colored solution is quantified by absorption at 570 nm by using a sweeping multi-cuvette spectrophotometer. The data concerning the proliferation is expressed in percentages of live cells in the treated wells, divided by the live cells in the control. Each point represents the average of three independent experiments, each experiment representing six determinations.

For the other cell lines (HCT15, LOVO, A549, A172, U373, U87), 1000 to 2000 cells are seeded in a well of a plaque of microwells 24 hours before the medicinal treatment. They are incubated with each of the compounds to be tested or their corresponding solvent (control) for 72.hours in a final concentration pool of $1 \cdot 10^{-10}$ to $1 \cdot 10^{-6}$ M.

The results are expressed in percentages of the proliferations calculated by the optical density of the cells treated with a medication divided by the OD of the control cells (cells treated with DMSO). As is represented in Table II, the compounds to be tested inhibited the proliferation of the cells as a function of dose.

TABLE II

Percentage of Cellular Proliferation

| Example | Cell lines | Concentration nM | | | | | | |
|---|---|---|---|---|---|---|---|---|
| 6 | | 0.1 | 1 | 10 | 100 | 1000 | 10000 | 100000 |
| Example 3 | L1210 | 87.22 | 68.92 | 42.64 | 26.85 | 10.83 | 2.11 | 2.20 |
| | HCT15 | 86.00 | 84.00 | 58.00 | 44.00 | 18.00 | 9.00 | 13.00 |
| | LOVO | 108.00 | 86.00 | 54.00 | 31.00 | 23.00 | 10.00 | 12.00 |
| | A549 | 132.00 | 111.00 | 75.00 | 39.00 | 35.00 | 10.00 | 11.00 |
| | A172 | 89.00 | 101.00 | 68.00 | 37.00 | 27.00 | 10.00 | 7.00 |
| | U373 | 99.00 | 98.00 | 40.00 | 24.00 | 17.00 | 13.00 | 9.00 |
| | U87 | 108.00 | 85.00 | 42.00 | 23.00 | 15.00 | 5.00 | 6.00 |
| Example 4 | L1210 | 92.14 | 97.14 | 91.08 | 86.28 | 46.79 | 27.80 | 8.09 |
| | HCT15 | 91.00 | 92.00 | 86.00 | 78.00 | 54.00 | 20.00 | 7.00 |
| | LOVO | 80.00 | 75.00 | 79.00 | 69.00 | 38.00 | 21.00 | 5.00 |
| | A549 | 71.00 | 76.00 | 71.00 | 56.00 | 26.00 | 22.00 | 12.00 |
| | A172 | 93.00 | 92.00 | 98.00 | 97.00 | 44.00 | 31.00 | 10.00 |
| | U373 | 86.00 | 85.00 | 89.00 | 63.00 | 30.00 | 16.00 | 2.00 |
| | U87 | 98.00 | 101.00 | 98.00 | 74.00 | 11.00 | 6.00 | 2.00 |
| Example 9 | L1210 | 74.04 | 62.05 | 44.72 | 34.01 | 20.20 | 4.34 | 1.58 |
| | HCT15 | 94.00 | 89.00 | 59.00 | 35.00 | 15.00 | 8.00 | 3.00 |
| | LOVO | 74.00 | 85.00 | 44.00 | 31.00 | 21.00 | 4.00 | 2.00 |
| | A549 | 91.00 | 88.00 | 50.00 | 31.00 | 23.00 | 5.00 | 3.00 |
| | A172 | 97.00 | 89.00 | 44.00 | 36.00 | 19.00 | 3.00 | 1.00 |
| | U373 | 89.00 | 69.00 | 24.00 | 18.00 | 8.00 | 3.00 | 1.00 |
| | U87 | 105.00 | 72.00 | 14.00 | 7.00 | 4.00 | 2.00 | 6.00 |
| Example 10 | L1210 | 91.51 | 97.94 | 89.28 | 67.32 | 31.51 | 19.78 | 3.65 |
| | HCT15 | 111.00 | 87.00 | 103.00 | 63.00 | 42.00 | 17.00 | 9.00 |
| | LOVO | 71.00 | 76.00 | 77.00 | 52.00 | 29.00 | 18.00 | 4.00 |
| | A549 | 71.00 | 76.00 | 71.00 | 56.00 | 36.00 | 22.00 | 7.00 |
| | A172 | 93.00 | 92.00 | 91.00 | 60.00 | 39.00 | 15.00 | 3.00 |
| | U373 | 96.00 | 104.00 | 87.00 | 35.00 | 20.00 | 10.00 | 2.00 |
| | U87 | 96.00 | 79.00 | 89.00 | 17.00 | 6.00 | 5.00 | 2.00 |
| Example 11 | L1210 | 91.99 | 81.37 | 23.16 | 16.38 | 5.59 | 1.45 | 1.04 |
| | HCT15 | 71.00 | 63.00 | 45.00 | 23.00 | 12.00 | 9.00 | 9.00 |
| | LOVO | 66.00 | 42.00 | 29.00 | 21.00 | 8.00 | 3.00 | 3.00 |
| | A549 | 82.00 | 44.00 | 29.00 | 26.00 | 4.00 | 3.00 | 2.00 |
| | A172 | 95.00 | 53.00 | 47.00 | 39.00 | 12.00 | 3.00 | 2.00 |
| | U373 | 50.00 | 30.00 | 25.00 | 8.00 | 2.00 | 1.00 | 2.00 |
| | U87 | 40.00 | 21.00 | 12.00 | 6.00 | 1.00 | 1.00 | 1.00 |

Test of Development in Vivo

The compounds according to the invention are tested in vivo using the lymphoblastic leukemia L1210 cell lines of mice. The tumor cells are maintained by a series of i.p. means in mice DBA/2 Lafacedu, Lyon, France). In an experimental trial, $10^6$ cells/0.2 ml are injected by i.p. passage into female B6D2F1 mice. The treatment begins day 1 after inoculation with leukemia and continues to day 4 or to day 8. The compounds to be tested are injected i.p. or i.v. in different concentrations and the volume injected is adjusted to 0.1 ml/10 g body weight. The non-treated mice die between day 9 and day 14, after the injection of lymphoblastic leukemia L1210 cells and survival of the treated mice is observed during an extended period of up to 60 days.

The experiment is conducted with 5-ethyl-4,5-dihydro-5-hydroxy-1H-oxepino[3'4':6,7]-indolizine[1,2-b]quinoline-3,15 (4H, 13H)-dione. This compound augments by 50% the duration of life of the mice at concentrations of between 0.32 and 2.5 mg/kg administered i.p. during 4 days and at concentrations of between 0.32 and 5.0 mg/kg administered i.v. for 8 days.

We claim:

1. A compound selected from the group consisting of enaniomeric, racemic mixtures or combinations thereof of a compound of the formula

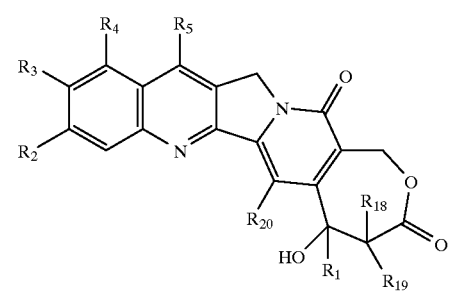

wherein $R_1$ is selected from the group consisting of alkyl of 1 to 6 carbon atoms, haloalkyl of 1 to 6 carbon atoms, lower alkenyl of up to 6 carbon atoms, alkoxyalkyl of 2 to 12 carbon atoms and alkylthio alkyl of 2 to 12 carbon atoms, $R_2$, $R_3$ and $R_4$ are independently selected from the group consisting of hydrogen, halogen, haloalkyl of 1 to 6 carbon atoms, alkyl of 1 to 6 carbon atoms, alkenyl of 2 to 6 carbon atoms, —CN, cyanoalkyl of 1 to 6 carbon atoms, —NO$_2$, nitroalkyl of 1 to 6 carbon atoms, —CONH$_2$, amidoalkyl of 1 to 6 carbon atoms, hydrazino, hydrazinoalkyl of 1 to 6 carbon atoms, azido, azidoalkyl of 1 to 6 carbon atoms,

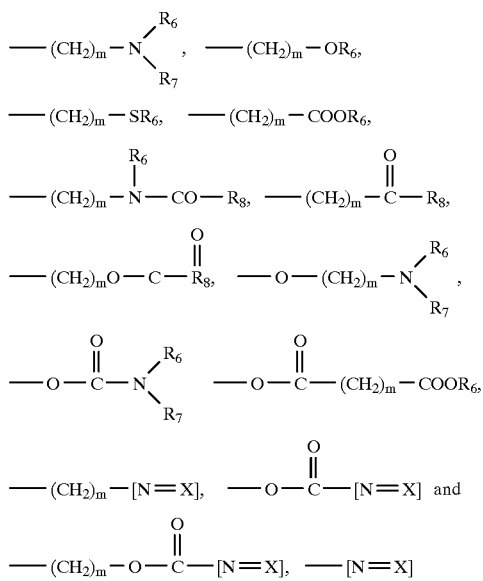

is a substituted or unsubstituted heterocyclic of 5 to 8 ring atoms with X being ring members selected from the group consisting of —O—, —S—, —CH$_2$—, —CH=, —N=,

—COR$_{10}$ and unsubstituted or substituted aryl, and aryl lower alkyl wherein the substituent is selected from the group consisting of alkyl of 1 to 6 carbon atoms, halogen, —NO$_2$, —NH$_2$, alkylamino of 1 to 6 carbon atoms, haloalkyl of 1 to 6 carbon atoms, hydroxyalkyl of 1 to 6 carbon atoms, alkoxy of 1 to 6 carbon atoms and lower alkoxy alkyl of 2 to 12 carbon atoms, R$_5$ is selected from the group consisting of hydrogen, halogen, halogen lower alkyl, lower alkyl, lower alkoxy, lower alkoxy lower alkyl, lower alkylthio lower alkyl, cycloalkyl, cycloalkyl lower alkyl, cyano, cyano alkyl, hydroxy lower alkyl, nitro, (CH$_2$)$_m$COR$_8$, (CH$_2$)$_m$NR$_6$COR$_8$, (CH$_2$)$_m$NR$_6$R$_7$, (CH$_2$)$_m$N(CH$_3$)(CH$_2$)$_n$NR$_6$R$_7$, (CH$_2$)$_m$OCOR$_8$, (CH$_2$)$_m$OCONR$_6$R$_7$, or substituted or unsubstituted (CH$_2$)$_m$[N=X], OCO [N=X], (CH$_2$)$_m$OCO [N=X], aryl or aryl lower alkyl; R$_6$ and R$_7$ are independently selected from the group consisting of hydrogen, alkyl of 1 to 6 carbon atoms, hydroxyalkyl of 1 to 6 carbon atoms, alkylaminoalkyl of 2 to 12 carbon atoms, aminoalkyl of 1 to 6 carbon atoms, cycloalkyl of 3 to 7 carbon atoms, cycloalkylalkyl of 4 to 13 carbon atoms, alkenyl of 2 to 6 carbon atoms, alkoxyalkyl of 2 to 12 carbon atoms, haloalkyl of 1 to 6 carbon atoms and substituted and unsubstituted aryl and arylalkyl of 1 to 6 alkyl carbon atoms and the substituent is at least one member of the group consisting of halogen, —NO$_2$, —NH$_2$, alkyl of 1 to 6 carbon atoms, alkylamino of 1 to 6 carbon atoms, haloalkyl of 1 to 6 carbon atoms, hydoxyalkyl of 1 to 6 carbon atoms, lower alkoxy of 1 to 6 carbon atoms and alkoxyalkyl of 2 to 12 carbon atoms, R$_8$ is selected from the group consisting of hydrogen, alkyl of 1 to 6 carbon atoms, hydroxyalkyl of 1 to 6 carbon atoms, —NH$_2$, alkylamino of 1 to 6 carbon atoms, alkylaminoalkyl of 2 to 12 carbon atoms, aminoalkyl of 1 to 6 carbon atoms, cycloalkyl of 3 to 7 carbon atoms, cycloalkylalkyl of 4 to 13 carbon atoms, alkenyl of 2 to 6 carbon atoms, alkoxy of 1 to 6 carbon atoms, alkoxyalkyl of 2 to 12 carbon atoms, haloalkyl of 1 to 6 carbon atoms and unsubstituted or substituted aryl and arylalkyl of 1 to 6 alkyl carbon atoms, the substituents being at least one member of the group consisting of alkyl of 1 to 6 carbon atoms, halogen, —NO$_2$, —NH$_2$, alkylamino of 1 to 6 carbon atoms, haloalkyl of 1 to 6 carbon atoms, hydroxyalkyl of 1 to 6 carbon atoms, alkoxy of 1 to 6 carbon atoms and alkoxyalkyl of 2 to 12 carbon atoms, R$_9$ is selected from the group consisting of hydrogen, alkyl of 1 to 6 carbon atoms, haloalkyl of 1 to 6 carbon atoms, aryl and aryl substituted with at least one member of the group consisting of the group consisting of halogen, alkyl of 1 to 6 carbon atoms, —NO$_2$, —NH$_2$, alkylamino of 1 to 6 carbon atoms, haloalkyl of 1 to 6 carbon atoms, hydroxyalkyl of 1 to 6 carbon atoms, alkoxy of 1 to 6 carbon atoms and akloxyalkyl of 2 to 12 carbon atoms, R$_{10}$ is selected from the group consisting of hydrogen, alkyl of 1 to 6 carbon atoms, haloalkyl of 1 to 6 carbon atoms, alkoxy of 1 to 6 carbon atoms and unsubstituted or substituted aryl with the substituents being at least one member of the group consisting of alkyl of 1 to 6 carbon atoms, haloalkyl of 1 to 6 carbon atoms, hydroxy alkyl of 1 to 6 carbon atoms and a alkoxyalkyl of 2 to 12 carbon atoms, R$_{18}$ and R$_{19}$ are independently selected from the group consisting of hydrogen, halogen, alkyl of 1 to 6 carbon atoms, alkoxy of 1 to 6 carbon atoms and —OH, R$_{20}$ is hydrogen or halogen, m is an integer from 0 to 6, n is 1 or 2 and their non-toxic, pharmaceutically acceptable acid addition salts.

2. A compound of claim 1 wherein R$_1$ is selected from the group consisting of alkyl of 1 to 6 carbon atoms, alkenyl of 2 to 6 carbon atoms, haloalkyl of 1 to 6 carbon atoms and alkoxyalkyl of 2 to 12 carbon atoms, R$_2$ R$_3$ and R$_4$ are independently selected from the group consisting of hydrogen, halogen, haloalkyl of 1 to 6 carbon atoms, alkyl of 1 to 6 carbon atoms, —NO$_2$, —CONH$_2$, amidoalkyl of 1 to 6 carbon atoms, hydrazino, hydrazinoalkyl of 1 to 6 carbon atoms, azido azidoalkyl of 1 to 6 carbon atoms,

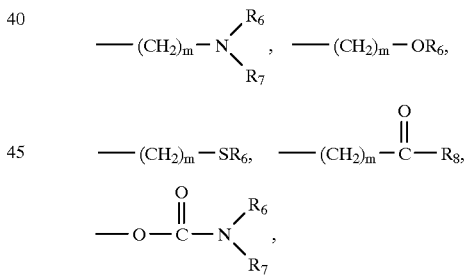

substituted or unsubstituted

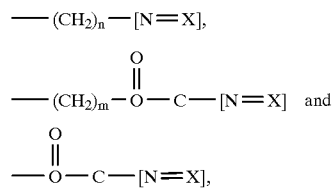

R$_5$ is selected from the group consisting of hydrogen, halogen, alkyl of 1 to 6 carbon atoms, haloalkyl of 1 to 6 carbon atoms, alkoxy of 1 to 6 carbon atoms, alkoxy alkyl of 2 to 12 carbon atoms, alkylthioalkyl of 2 to 12 carbon atoms, hydroxyalkyl of to 6 carbon atoms,

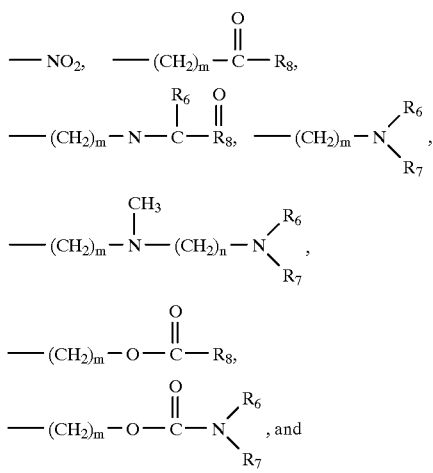

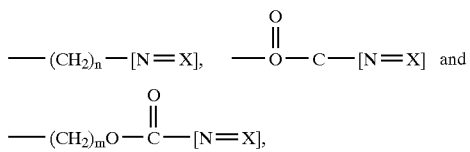

substituted or unsubstituted

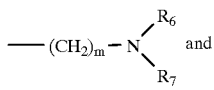

$R_6$ and $R_7$ are individually selected from the group consisting of hydrogen, alkyl of 1 to 6 carbon atoms, hydroxyalkyl of 1 to 6 carbon atoms, alkylaminoalkyl of 2 to 12 carbon atoms, aminoalkyl of 1 to 6 carbon atoms, cycloalkyl of 3 to 7 carbon atoms, cycloalkylalkyl of 4 to 13 carbon atoms, alkoxyalkyl of 2 to 12 carbon atoms, haloalkyl of 1 to 6 carbon atoms, aryl and aralkyl of 1 to 6 alkyl carbon atoms, $R_8$ is selected from the group consisting of hydrogen, alkyl of 1 to 6 carbon atoms, hydroxyalkyl of 1 to 6 carbon atoms, alkylamino of 1 to 6 carbon atoms, alkylaminoalkyl of 2 to 12 carbon atoms, aminoalkyl of 1 to 6 carbon atoms, cycloalkyl of 3 to 7 carbon atoms, cycloalkylalkyl of 4 to 13 carbon atoms, alkenyl of 2 to 6 carbon atoms, alkoxy of 1 to 6 carbon atoms, alkoxyalkyl of 2 to 12 carbon atoms, haloalkyl of 1 to 6 carbon atoms and aryl and arylalkyl of 1 to 6 alkyl carbon atoms, $R_9$ is selected from the group consisting of hydrogen, alkyl of 1 to 6 carbon atoms and haloalkyl of 1 to 6 carbon atoms, $R_{10}$ is selected from the group consisting of hydrogen, alkyl of 1 to 6 carbon atoms, haloalkyl of 1 to 6 carbon atoms and alkoxy of 1 to 6 carbon atoms and $R_{18}$, $R_{19}$ and $R_{20}$ are hydrogen.

3. A compound of claim 2 where $R_1$ is ethyl.

4. A compound of claim 3 wherein $R_2$ and $R_3$ are independently selected from the group consisting of hydrogen, alkyl of 1 to 6 carbon atoms, halogen, haloalkyl of 1 to 6 carbon atoms and —$(CH_2)_m$—$OR_6$ and $R_4$ and $R_5$ are independently selected from the group consisting of hydrogen, alkyl of 1 to 6 carbon atoms,

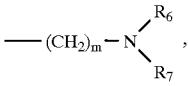

substituted or unsubstituted —$(CH_2)_n$—N=X wherein said substituent is alkyl of 1 to 6 carbon atoms.

5. A compound of claim 4 wherein $R_4$ is hydrogen or

—$(CH_2)_m$—N$\begin{smallmatrix}R_6\\R_7\end{smallmatrix}$ , $R_6$ and $R_7$ are independently hydrogen or alkyl of 1 to 6 carbon atoms, $R_5$ is selected from the group consisting of hydrogen, alkyl of 1 to 6 carbon atoms and optionally substituted—$(CH_2)_n$—N=X when the substituent is alkyl of 1 to 6 carbon atoms and —N=X is selected from the group consisting of piperazinyl, piperidyl and morpholinyl.

6. A compound of claim 5 wherein $R_2$ is hydrogen or halogen, $R_3$ is selected from the group consisting of hydrogen, halogen, alkyl of 1 to 6 carbon atoms and —$OR_6$ and $R_6$ is selected from the group consisting of hydrogen, alkyl of 1 to 6 carbon atoms and aralkyl of 1 to 6 carbon atoms.

7. A compound of claim 6 wherein $R_2$ is selected from the group consisting of hydrogen, chlorine and fluorine and $R_3$ is selected from the group consisting of hydrogen, fluorine, chlorine, methyl and methoxy.

8. A compound of claim 7 wherein $R_4$ is hydrogen and $R_5$ is hydrogen or substituted —$(CH_2)_n$-piperidyl optionally substituted with alkyl of 1 to 6 carbon atoms.

9. A compound of claim 6 wherein $R_2$ is selected from the group consisting of chlorine and fluorine and $R_3$ is selected from the group consisting of fluorine and methyl.

10. A compound of claim 9 characterized in that it is 5-ethyl- 9,10-difluoro-4,5-dihydro-5-hydroxy-1H-oxepino-[3':4']indolizino[1,2-b]quinoline-3,15[4H, 13H]dione.

11. A compound of claim 4 selected from the group consisting of -5-ethyl-4,5-dihydro-5-hydroxy-1H-oxepino [3',4':6,7]-indolizine [1,2-b] quinoline-3,15 (4H,13H)-dione 5,12-diethyl-4,5-dihydro-5-hydroxy-1H-oxepino [3'4':6,7]-indolizine [1,2-b] quinoline-3,15[(4H,13H)-dione-10-benzyloxy-5-ethyl-4,5-dihydro-5-hydroxy-1H-oxepino [3',4':6,7]-indolizino (1,2-b]-quinoline-3,15 (4H,13H)-dione-5-ethyl-4,5-dihydro-5,10,-dihyroxy-1H-oxepino [3'4':6,7]-indolizino [1,2-b] quinoline-3,15 (4H,13H)-dione 11-(dimethylamino) -methyl-5-ethyl-4,5-dihydro-5-10-dihydroxy-1H-oxepino[3',4':6.7]-indolizino [1,2-b] quinoline-3,15 (4H-13H)-dione 5-ethyl-9-fluoro-4,5-dihydro-5-hydroxy-10-methoxy-1H-oxepino [3',4':6.7] indolizino [1,2-b] quinoline-3,15(4H,13H)-dione 9-chloro-5-ethyl-4,5-dihydro-5-hydroxy-10-methyl-1H-oxepino [3'4':6.7]indolizino [1,2-b] quinoline-3,15(4H,13H)-dione 5-ethyl-9,10-difluoro-4,5-dihydro-5-hydroxy-1H-oxepino [3'4':6,7] indolizino [1,2-b]quinoline-3,15(4H,13H)-dione 9-chloro-5-ethyl-4,5-dihydro-5-hydroxy-10-methoxy-4H-oxepino [3'4':6.7] indolizino [1,2-b] quinoline-3,15(4H, 13H)-dione 5-ethyl-4,5-dihydro-5-hydroxy-10-methoxy-1H-oxepino [3'4':6,7] indolizino [1,2-b]quinoline-3,15(4H, 13H)-dione 9-11-dichloro-5-ethyl-4,5-dihydro-5-hydroxy-1H-oxepino [3'4':6,7] indolizino [1,2-b]quinoline-3,15(4H, 13H)-dione 5-ethyl-9-fluoro-4,5-dihydro-5-hydroxy-10-methyl-1H-oxepino [3'4':6,7] indolizino[1,2-b]quinoline-3, 15(4H,13H)-dione 5-ethyl-10-fluoro-4,5-dihydro-5-hydroxy-1H-oxepino [3'4':6,7] indolizino[1,2-b] quinoline-3,15(4H,13H)-dione 10-chloro-5-ethyl-4,5-dihydro-5-hydroxy-1H-oxepino [3'4':6,7] indolizino [1,2-b] quinoline-3,15(4H,13H)-dione 10-chloro-5-ethyl-9-fluoro-4,5-dihydro-5-hydroxy-1H-oxepino [3'4':6,7] indolizino [1,2-b] quinoline-3,15(4H-13H)-dione 5,12-diethyl-4,5-dihydro-5, 10 dihydroxy 11 morpholino methyl-1H-oxepino [3'4':6,7] indolizino [1,2-b] quinoline 3,15(4H,13H) -dione 5,12- diethyl-9-fluoro-4,5-dihydro 5 hydroxy-10-methoxy-1H-oxepino [3'4':6,7] indolizino [1,2-b] quinoline-3,15(4H-13H)-dione 5-ethyl-4,5-dihydro-5-hydroxy-12-methyl-1H-oxepino [3'4':6,7] indolizino [1,2-b] quinoline-3,15(4H,13H)-dione 9-chloro-5-ethyl-4,5-dihydro-5-hydroxy-10-methoxy-12-(4-methyl piperazinomethyl)-1H-oxepino [3'4':6,7] indolizino [1,2-b] quinoline-3,15(4H,13H)-dione 9-chloro-5-ethyl-4,5-dihydro-5-hydroxy-10-methoxy-12-morpholinomethyl-1H-oxepino [3'4':6,7] indolizino [1,2b] quinoline 3,15(4H,13H)-dione 5-ethyl-4,5-dihydro-5-hydroxy-12-(4-methyl piperazinomethyl)-1H-oxepino [3'4':6,7] indolizino [1,2-b] quinoline-3,15(4H,13H) -dione 5-ethyl-4,5-dihydro-5-hydroxy-12-piperidinomethyl-1H-oxepino [3'4':6,7] indolizino [1,2-b] quinoline-3,15 (4H, 13H)-dione 5-ethyl-4,5-dihydro-5-hydroxy-12-morpholinomethyl-1H-oxepino [3'4':6,7] indolizino [1,2-b] quinoline-3,15(4H,13H)-dione 5-ethyl-10-fluoro-4,5-dihydro-5-hydroxy-12-(4-methylpiperazinomethyl)-1H-oxepino [3'4':6,7] indolizino [1,2-b] quinoline-3,15(4H, 13H)-dione 5-ethyl-10-fluoro-4,5-dihydro-5-hydroxy-12-morpholinomethyl-1H-oxepino [1,2-b] quinoline-3,15 (4H,13H)-dione 5-ethyl-9-fluoro-4,5-dihydro-5-hydroxy-10-methyl-12-(4-methylpiperazinomethyl)-1H-oxepino [3'4':6,7] indolizino [1-2b] quinoline-3,15(4H,13H)-dione 5-ethyl-9-fluoro-4,5-dihydro-5-hydroxy-10-methyl-12-morpholinomethyl-1H-oxepino [3'4':6,7] indolizino [1,2-b] quinoline-3,15(4H, 13H)-dione 5-ethyl-9-fluoro-4,5-dihydro-5-hydroxy-10-methyl-12-piperidinomethyl-1H-oxepino [3'4':6,7] indolizino [1-2b] quinoline3,15(4H, 13H) -dione 9-chloro-5-ethyl-10-fluoro-4,5-dihydro-5-hydroxy-12-morpholinomethyl-1H-oxepino [3'4':6,7] indolizino [1-2b] quinoline-3,15(4H,13H)-dione and their non-toxic, pharmaceutically acceptable salt.

12. A method of inhibiting to poisomerase in warm-blooded animals comprising administering to warm-blooded animals an amount of a compound of claim 1 sufficient to inhibit to poisomerase activity.

13. A method of inhibiting tumor in warm-blooded animals compound comprising administering a tumor growth inhibiting amount of a of claim 1.

* * * * *